(12) United States Patent
Polasek (10) Patent No.: US 12,215,064 B2
(45) Date of Patent: Feb. 4, 2025

(54) COMPOUNDS FOR CHROMATOGRAPHIC SEPARATION OF RARE EARTH ELEMENTS AND S-, P-, D-METALS, METHOD OF SEPARATION, AND USE THEREOF

(71) Applicant: USTAV ORGANICKE CHEMIE A BIOCHEMIE AV CR, V.V.I, Prague (CZ)

(72) Inventor: Miloslav Polasek, Prague (CZ)

(73) Assignee: USTAV ORGANICKE CHEMIE A BIOCHEMIE AV CR, V.V.I., Prague (CZ)

( * ) Notice: Subject to any disclaimer, the term of this patent is extended or adjusted under 35 U.S.C. 154(b) by 658 days.

(21) Appl. No.: 17/616,340

(22) PCT Filed: May 28, 2020

(86) PCT No.: PCT/CZ2020/050035
§ 371 (c)(1),
(2) Date: Dec. 3, 2021

(87) PCT Pub. No.: WO2020/244686
PCT Pub. Date: Dec. 10, 2020

(65) Prior Publication Data
US 2022/0259119 A1 Aug. 18, 2022

(30) Foreign Application Priority Data
Jun. 5, 2019 (EP) ..................................... 19178492

(51) Int. Cl.
*C07D 401/06* (2006.01)
*B01D 15/42* (2006.01)
(Continued)

(52) U.S. Cl.
CPC .......... *C07B 59/002* (2013.01); *B01D 15/424* (2013.01); *C07D 401/06* (2013.01);
(Continued)

(58) Field of Classification Search
CPC . C07B 59/002; C07B 2200/05; B01D 15/424; C07D 401/06; C07D 401/14; C07F 9/6524
See application file for complete search history.

(56) References Cited

U.S. PATENT DOCUMENTS 5,756,065 A 5/1998 Wilson et al.

FOREIGN PATENT DOCUMENTS

JP S62-145164 6/1987
WO WO-94/26275 A1 11/1994
(Continued)

OTHER PUBLICATIONS

Bilewicz et al: "Synthesis and redox properties of a copper(II) complex of N,N', N''', N'''-tetrakis (2 quinolinemethyl-1-oxide)-1,4,8, 11-tetraazacyclotetradecane", POLYHEDRON. , vol. 9, No. 19, Jan. 1, 1990 (Jan. 1, 1990), pp. 2353-2357, XP055638470, GB, ISSN: 0277-5387, DOI: 10.1016/50277-5387(00)86813-8.
(Continued)

*Primary Examiner* — Timothy R Rozof
(74) *Attorney, Agent, or Firm* — FOLEY & LARDNER LLP (57) ABSTRACT

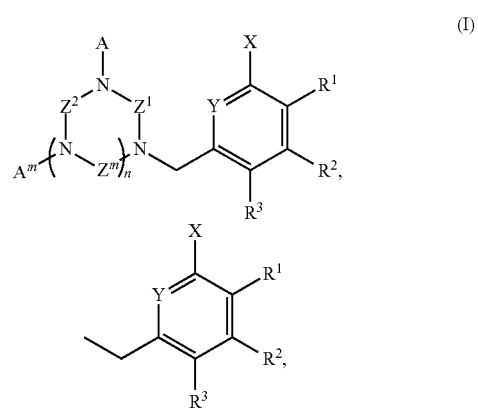

The present invention relates to compounds of general formula (I), wherein —X is selected from a group consisting of H; $C_1$ to $C_6$, alkyl; halogen (F, Cl, Br or I); Y is selected from a group consisting of nitrogen; N-oxide; $Z^1$, $Z^2$, $Z^m$, wherein m is 1 or 2, are independently selected from the group consisting of —$CH_2$—$CH_2$— and —$CH_2$—$CH_2$—$CH_2$; A, $A^m$, wherein m is 1 or 2, are independently selected from H; —$CH_2COOH$; —$CH_2C(O)NH_2$; —$CH_2P(O)(OH)_2$, and n is 1 or 2; $R^1$, $R^2$, $R^3$ are independently H; $C_1$ to $C_6$, alkyl; $C_1$ to $C_6$ alkyloxy; $C_6$ to $C_{10}$ aryloxy; benzyloxy; $C_1$ to $C_6$ alkylthio; $C_6$ to $C_{10}$ arylthio; F; Cl; Br; I; OH; SH; $NH_2$; $C_1$ to $C_6$, alkylamino; di($C_1$ to $C_6$, alkyl)amino; $C_1$ to $C_6$ acylamino; di($C_1$ to $C_6$ acyl) amino; $C_6$ to $C_{10}$ arylamino; di($C_6$ to $C_{10}$ aryl)amino; CN; OH; nitro; $COOR_n$, $C(O)NHR_n$, $C(O)N(R_n)_2$, wherein $R_n$ is independently H or $C_1$ to $C_{10}$ alkyl or $C_6$, to $C_{10}$ aryl; and/or neighboring two of $R^1$, $R^2$, $R^3$ together with neighboring two carbon atoms of the aromatic cycle form a six-membered ring, optionally substituted with one or more substituents independently selected from the group consisting of OH, SH, $CF_3$, F, Cl, Br, I, $C_1$ to $C_6$, alkyl, $C_1$ to $C_6$, alkyloxy, $C_1$ to $C_6$ alkylthio, $NH_2$, $C_1$ to $C_6$ alkylamino, di($C_1$ to $C_6$ alkyl)amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl; with the proviso that when n is 2 and all of $Z^1$, $Z^2$, $Z^m$ are —$CH_2$—$CH_2$—, then A is not —$CH_2COOH$; for chromatographic separation of rare earth elements and/or s-, p- and d-block metals, as well as to the method of the separation of rare earth elements.

18 Claims, 1 Drawing Sheet

(51) Int. Cl.
  *C07B 59/00* (2006.01)
  *C07D 401/14* (2006.01)
  *C07F 9/6524* (2006.01)

(52) U.S. Cl.
  CPC .......... *C07D 401/14* (2013.01); *C07F 9/6524* (2013.01); *C07B 2200/05* (2013.01)

(56) References Cited

FOREIGN PATENT DOCUMENTS

| WO | WO-95/01346 A1 | 1/1995 |
| WO | WO-2012/155076 A2 | 11/2012 |
| WO | WO-2015/051362 A1 | 4/2015 |
| WO | WO-2015/083292 | 6/2015 |

OTHER PUBLICATIONS

Database Caplus [Online] Chemical Abstracts Service, Columbus, Ohio, US; 1990, XP002795384, retrieved from STN Database accession No. 1990:451380.
Gaudette et al. "pH-Dependent spin state population and 19 F NMR chemical shift via remote ligand protonation in an iron(II) complex", Commun. Chem. Commun, vol. 53, No. 53, Jan. 1, 2017 (Jan. 1, 2017), pp. 12962-12965, XP55638565, DOI: 10.1039/c7cc08158h.
Kifle D. et al., Selective liquid chromatographic separation of yttrium from heavier rare earth elements using acetic acid as a novel eluent, Journal of Chromatography A, 2013, No. 1307, p. 86-90.
Kong et al: "Synthesis and crystal l structure of nickel and cobalt complexes with tetraazamacrocyclic ligand attached four dangling pyridinyl groups", Inorganic Chemistry Communications., vol. 7, No. 2, Feb. 1, 2004 (Feb. 1, 2004), pp. 195-200, XP055638573, NL, ISSN: 1387-7003, DOI: 10.1016/j.inoche.2003.05.001.
Nonat et al: "Structural and Photophysical Studies of Highly Stable Lanthanide Complexes of Tripodal 8-Hydroxyquinolinate Ligands Based on 1,4,7-Triazacyclononane", Inorganic Chemistry, vol. 48, No. 9, May 4, 2009 (May 4, 2009), pp. 4207-4218, XP055638497, Easton, US ISSN: 0020-1669, DOI: 10.1021/ic9000076.
Tsitovich et al: "Fe(II) and Co(II) N-methylated CYCLEN complexes as paraSHIFT agents with large temperature dependent shifts", Dalton Transactions, vol. 47 No. 3, Jan. 1, 2018 (Jan. 1, 2018), pp. 916-924, XP055638560, ISSN: 1477-9226, DOI: 10.1039/C7DT03812G.
Aime et al, "Structure and relaxivity of macrocyclic gadolinium complexes incorporating pyridyl and 4-morpholinopyridyl substituents", New Journal of Chemistry, Royal Society of Chemistry, GB, vol. 23, No. 7, Jan. 1, 1999 (Jan. 1, 1999), pp. 669-670.
Examination Report for EP Application No. 19178492.5 DTD Aug. 30, 2021, 3 pages.
Gempf et al., "Direct and selective tagging of cysteine residues in peptides and proteins with 4-nitropyridyl lanthanide complexes", Chemical Communications, vol. 49, No. 80, Jan. 1, 2013 (Jan. 1, 2013), pp. 9104-9104.
Hanaoka et al., "Time-Resolved Long-Lived Luminescence Imaging Method Employing Luminescent Lanthanide Probes with a New Microscopy System", Journal of the American Chemical Society, vol. 129, No. 44, Nov. 1, 2007 (Nov. 1, 2007), pp. 13502-13509.
International Preliminary Report on Patentability for PCT Patent Application No. PCT/CZ2020/050035 dated Apr. 14, 2021 (6 pages).
International Search Report and Written Opinion on PCT Patent Application No. PCT/CZ2020/050035 dated Jun. 30, 2020 (13 pages).
Laznickova et al., "Mono(pyridine-N-oxide)DOTA analog and its G1/G4-PAMAM dendrimer conjugates labeled with 177Lu: Radiolabeling and biodistribution studies", Applied Radiation and Isotopes, vol. 84, Feb. 1, 2014 (Feb. 1, 2014), pp. 70-77.
Mason et al., "PARASHIFT Probes: Solution NMR and X-ray Structural Studies of Macrocyclic Ytterbium and Yttrium Complexes", Inorganic Chemistry, vol. 56, No. 7, Mar. 15, 2017 (Mar. 15, 2017), pp. 4028-4038.
Polasek et al., "Is Macrocycle a Synonym for Kinetic Inertness in Gd(III) Complexes? Effect of Coordinating and Noncoordinating Substituents on Inertness and Relaxivity of Gd(III) Chelates with DO3A-like Ligands", Inorganic Chemistry, vol. 52, No. 7, Mar. 21, 2013 (Mar. 21, 2013), pp. 4084-4096.
Pollet et al., "Proton Exchange in a Paramagnetic Chemical Exchange Saturation Transfer Agent from Experimental Studies and ab Initio Metadynamics Simulation" Inorganic Chemistry, vol. 56, No. 8, Mar. 27, 2017 (Mar. 27, 2017), pp. 4317-4323.
Regueiro-Figueroa et al., "Highly Stable Complexes of Divalent Metal Ions (Mg 2 , Ca2 , Cu2 , Zn2 , Cd2 , and Pb2 ) with a Dota-Like Ligand Containing a Picolinate Pendant: Complexes of Dota-Like Ligand Containing a Picolinate Pendant", European Journal of Inorganic Chemistry—Chemische Berichte, vol. 2014, No. 36, Nov. 13, 2014 (Nov. 13, 2014), pp. 6165-6173.
Tsebrikova et al., "Cyclen-containing phosphonic acids as components of osteotropic68Ga radiopharmaceuticals", Russian Journal of General Chemistry, Maiknauka-Interperiodica, RU, vol. 85, No. 9, Oct. 21, 2015 (Oct. 21, 2015), pp. 2071-2079.
Xie, F., et al., "A critical review on solvent extraction of rare earths from aqueous solutions", Minerals Engineering, vol. 56, Feb. 1, 2014 (Feb. 1, 2014), pp. 10-28.

COMPOUNDS FOR CHROMATOGRAPHIC SEPARATION OF RARE EARTH ELEMENTS AND S-, P-, D-METALS, METHOD OF SEPARATION, AND USE THEREOF

CROSS-REFERENCE TO RELATED APPLICATIONS

This application is a U.S. National Phase Application under 35 U.S.C. § 371 of International Application No. PCT/CZ2020/050035, filed on May 28, 2020, which claims the benefit of priority to EP application Ser. No. 19/178, 492.5, filed on Jun. 5, 2019, the contents of each of which are herein incorporated by reference.

TECHNICAL FIELD

This invention relates to compounds suitable for chromatographic separation of rare earth elements and/or s-, p-, d-block metals, a method of chromatographic separation of rare earth elements and/or s-, p-, d-block metals from a mixture of metal ions, at least one of them being a rare earth metal selected from Ce, Dy, Er, Eu, Gd, Ho, La, Lu, Nd, Pr, Pm, Sm, Sc, Tb, Tm, Yb and Y, alkaline earth metal, Al, Ga, In, Tl, Sn, Pb or transitional metal, and use thereof for extraction and separation of rare earth metals and/or s-, p-, d-block metals from mixtures.

BACKGROUND ART

Radionuclides of metal elements are increasingly used in nuclear medicine, mainly for diagnosis and therapy of oncological diseases. There is a growing interest in targeted radiotherapy that uses a targeting vector (peptide, antibody, etc.) to deliver the radioactive payload specifically to cancer tissue. Radionuclides of metal elements are advantageous because the connection to the targeting vector can be conveniently achieved through coordination to a bifunctional chelator.

To reduce the possibility of unwanted toxicity and to maximize efficiency of the treatment, radionuclides for medical applications are preferred in a so-called "no-carrier-added" (NCA) form, i.e. containing no unnecessary matter. However, achieving this extremely high purity of metal radionuclides is a major challenge. Most commonly, medical radionuclides are prepared from a stable nuclide by a particle-induced nuclear reaction. Preparation of NCA radionuclide requires complete removal of the parent nuclide and byproducts, both usually present in several orders of magnitude larger quantities. Contamination with trace metals from solvents, chemicals and equipment must be strictly avoided. Furthermore, handling radioactivity brings many technical difficulties. Common separation methods are either not practical for work with radioactivity or not efficient enough to provide NCA radionuclides. New separation methods specifically designed for metal radionuclides are needed.

Rare earth elements (scandium—Sc, yttrium—Y, lanthanum—La, cerium—Ce, praseodymium—Pr, neodymium—Nd, promethium—Pm, samarium—Sm, europium—Eu, gadolinium—Gd, terbium—Tb, dysprosium—Dy, holmium—Ho, erbium—Er, thulium—Tm, ytterbium—Yb and lutetium—Lu) are a group of metals that offer a broad choice of radionuclides for medical applications. Radionuclides $^{90}$Y and $^{153}$Sm are approved by FDA, clinical trials are ongoing with $^{166}$Ho and $^{177}$Lu, and others show advantageous properties ($^{44}$Sc, $^{47}$Sc, $^{86}$Y, $^{149}$Pm, $_{159}$Gd, $^{149}$Tb, $^{161}$Tb, $^{165}$Dy, $^{161}$Ho, $^{169}$Er and $^{175}$Yb). These metals are chemically similar, providing the advantage that the same targeting vector, bioconjugation and labelling chemistry can be used with any member of the group. However, obtaining these radionuclides as NCA is notoriously difficult, as it usually requires separation of two neighboring rare earth elements with extremely similar properties.

The techniques so far applied to separation of rare earth radionuclides are ion exchange chromatography, extraction chromatography and liquid-liquid extraction (Nayak D., Lahiri S. (1999), Solvent Extr. Ion Exch. 17(5), 1133-1154). These techniques take advantage of small differences in the ionic radii that almost linearly decrease from $La^{3+}$ to $Lu^{3+}$. The ionic radius influences basicity and steric demands of the ions, properties that are used in the separation process. A common feature of these separation techniques is that the rare earth ion is involved in relatively weak interactions that allow rapid exchange of its immediate surrounding. These interactions include ionic interactions, solvation and coordination. As the molecular interactions are repeated many times during the exchange process, even small differences in properties between the metal ions are amplified, ultimately leading to separation. It is important to note that the coordinating ligands used in these techniques provide kinetically labile complexes with the rare earth ions to allow the exchange. Typical examples of such ligands are di-(2-ethylhexyl)phosphoric acid (HDEHP) and α-hydroxyisobutyric acid (α-HIBA) (Xie, F. et al. (2014), Miner. Eng. 56, 10-28). Strongly chelating ligands such as those derived from 1,4,7,10-tetraazacyclododecane (cyclen) are not used, because these provide kinetically inert complexes that do not permit the exchange (a typical example of such strong chelators is 1,4,7,10-tetraazacyclododecane-1,4,7,10-tetraacetic acid (DOTA)).

There are also alternative separation techniques that take advantage of more exotic oxidation states (other than 3+) of rare earth elements, but these are limited to the very few cases where such oxidation states are possible (Nayak D., Lahiri S. (1999), Solvent Extr. Ion Exch. 17(5), 1133-1154).

The techniques for separation of radionuclides of s-, p- and d-block metals are similar to those mentioned above for rare earth elements. Most commonly used are ion exchange chromatography, extraction chromatography and liquid-liquid extraction (Dietz M. L., Horwitz E. P. (2000), Ind. Eng. Chem. Res. 39(9), 3181-3188). Less commonly also precipitation, distillation and electrochemical deposition.

Typically, no single technique can provide satisfactory result and a combination of techniques must be used, with ion exchange chromatography or extraction chromatography as the last step (Medvedev D. G. et al. (2012), Appl. Radiat. Isot. 70(3), 423-429). The use of a single technique for the separation greatly simplifies the overall process and is highly desired. Also for these metals, strongly chelating ligands such as those derived from 1,4,7,10-tetraazacyclododecane (cyclen) are not used.

The need for an effective and fast separation of rare earth elements and s-, p- and d-block metals therefore remains.

DISCLOSURE OF THE INVENTION

Even though the state of the art teaches away from use of strong chelators for rare earth elements separation, surprisingly we have found that certain strong chelators are extremely efficient in such separations, and, moreover, they can also be used for s-, p-, d-block metals separations. s-, p-, d-metals are defined as metals belonging into groups II.A (alkaline earth metals), III.A (Al, Ga, In, Tl) and IV.A (Sn, Pb) and transitional metals (I.B to VIII.B group). The present invention relates to new types of chelators, and to a method of their use for separation of rare earth elements and/or s-, p-, d-block metals. The principle of separation is notably different from the abovementioned existing separation techniques, and provides simplified (and therefore faster) manipulation with rare earth and/or s-, p-, d-block metal radionuclides in solution, their processing and purification. The speed and simplicity of the method is crucial for manipulation with radionuclides, which undergo the radioactive decay. When bound to rare earth ions and/or s-, p-, d-block metals, the chelators of the present invention respond to even very small differences in the ionic radii of the metals by pronounced differences in polarity of the respective resulting chelates. Because of the varying polarity, the chelates can be separated by conventional chromatography on normal or reversed phase. The metals are thus separated in the form of chelates. Importantly, the chelators disclosed in this invention form chelates that are kinetically inert on the time-scale of the separation process. The kinetic inertness effectively protects the radionuclide from additional contamination with other metals, as the radionuclide cannot escape from the chelate nor can it be replaced by another metal ion during the chromatography. Importantly, this property allows using conventional chromatographic columns and instrumentation that consist of metal parts. The separation method of the present invention can be used to separate rare earth elements regardless of the particular isotopes of the involved elements.

The subject of the present invention is the use of compounds of general formula (I)

for chromatographic separation of rare earth elements and/or s-, p- and d-block metals,
wherein
X is selected from a group consisting of H; $C_1$ to $C_6$ alkyl; halogen (F, Cl, Br or I);
Y is selected from a group consisting of nitrogen; N-oxide;
$Z^1, Z^2, Z^m$, wherein m is 1 or 2, are independently selected from the group consisting of $-CH_2-CH_2-$ and $-CH_2-CH_2-CH_2-$;
A, $A^m$, wherein m is 1 or 2, are independently selected from H; $-CH_2COOH$; $-CH_2C(O)NH_2$; $-CH_2P(O)(OH)_2$, and n is 1 or 2;
$R^1, R^2, R^3$ are independently H; $C_1$ to $C_6$ alkyl; $C_1$ to $C_6$ alkyloxy; $C_6$ to $C_{10}$ aryloxy; benzyloxy; $C_1$ to $C_6$ alkylthio; $C_6$ to $C_{10}$ arylthio; F; Cl; Br; I; OH; SH; $NH_2$; $C_1$ to $C_6$ alkylamino; di($C_1$ to $C_6$ alkyl)amino; $C_1$ to $C_6$ acylamino; di($C_1$ to $C_6$ acyl)amino; $C_6$ to $C_{10}$ acylamino; di($C_6$ to $C_{10}$ aryl)amino; CN; OH; nitro; $COOR_n$, $C(O)NHR_n$, $C(O)N(R_n)_2$, wherein $R_n$ is independently H or $C_1$ to $C_{10}$ alkyl or $C_6$ to $C_{10}$ aryl;

and/or neighboring two of $R^1, R^2, R^3$ together with neighboring two carbon atoms of the aromatic cycle form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl)amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl;

with the proviso that when n is 2 and all of $Z^1, Z^2, Z^m$ are $-CH_2-CH_2-$, then A is not $-CH_2COOH$.

Rare earth elements are defined as cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) and yttrium (Y). s-, p- and d-block metals are preferably II.A, III.A, IV.A, V.A metals and transitional metals, more preferably II.A, III.A (Al, Ga, In, Tl), IV.A (Sn, Pb), V.A (Bi), I.B, II.B, and VIII.B group metals, most preferably selected from $Ca^{2+}$, $Fe^{2+}$, $Fe^{3+}$, $Co^{2+}$, $Ni^{2+}$, $Cu^{2+}$, $Zn^{2+}$, $Al^{3+}$, $Pb^{2+}$, $Bi^{3+}$.

The chromatographic separation of rare earth elements and/or s-, p- and d-block metals is defined as separation of any one of the above mentioned rare earth elements and/or s-, p- and d-block metals from a mixture of two or more metal ions, at least one of them being a rare earth element and/or s-, p- and d-block metal.

The general formula (I) of the present invention is meant to include all isomers, enantiomers and diastereoisomers.

In one preferred embodiment, the use according to the present invention relates to chromatographic separation of rare earth elements, thus selected from cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) and yttrium (Y).

In one preferred embodiment, the use according to the present invention relates to chromatographic separation of s-, p- and d-block metals, selected from groups II.A, III.A, IV.A, V.A, transitional metals (such as I.B, II.B, and VIII.B), preferably selected from $Ca^{2+}$, $Fe^{2+}$, $Fe^{3+}$, $Co^{2+}$, $Ni^{2+}$, $Cu^{2+}$, $Zn^{2+}$, $Al^{3+}$, $Pb^{2+}$, $Bi^{3+}$.

In one preferred embodiment of the use according to the present invention, X is selected from a group consisting of H; $-CH_3$ and Cl.

In one preferred embodiment of the use according to the present invention, $R^1, R^2, R^3$ are independently H; $C_1$ to $C_6$ alkyl; and/or neighboring two of $R^1, R^2, R^3$ together with neighboring two carbon atoms of the aromatic cycle form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl)amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl.

In one preferred embodiment of the use according to the present invention, at least two of A, A''' are —CH$_2$COOH and/or —CH$_2$P(O)(OH)$_2$.

In one embodiment of the use according to the present invention, at most one of A, A''' is H.

In one preferred embodiment of the use according to the present invention, X is —CH$_3$ or Cl, Y is nitrogen, and all of R$^1$, R$^2$, R$^3$ are H.

In another preferred embodiment of the use according to the present invention, X is H, Y is N-oxide, and two of R$^1$, R$^2$, R$^3$ together with neighboring two carbon atoms of the aromatic cycle form a six-membered ring, optionally substituted with one or more substituents independently selected from the group consisting of OH, SH, CF$_3$, F, Cl, Br, I, C$_1$ to C$_6$ alkyl, C$_1$ to C$_6$ alkyloxy, C$_1$ to C$_6$ alkylthio, NH$_2$, C$_1$ to C$_6$ alkylamino, di(C$_1$ to C$_6$ alkyl)amino, NO$_2$, COOH, COOR$_n$, C(O)NHR$_n$, C(O)N(102, wherein R$_n$ is independently H or C$_1$ to C$_{10}$ alkyl or C$_6$ to C$_{10}$ aryl.

In one embodiment of the use according to the present invention, R$^1$, R$^2$, R$^3$ are independently selected from H, OH, OCH$_3$, NO$_2$, F, Cl, Br, I, CH$_3$, COOH, COOR$_n$, C(O)NHR$_n$, C(O)N(R$_n$)$_2$, wherein R$_n$ is defined as above.

Preferably, the ring containing Y atom is selected from isoquinoline N-oxide, quinoline N-oxide, isoquinoline, quinoline, pyridine, pyridine N-oxide; more preferably, the ring containing Y atom is a pyridine ring, quinoline N-oxide or isoquinoline N-oxide.

In one preferred embodiment of the use according to the present invention, compounds of general formula (I) are selected from the group consisting of:

1-((4,7-bis(carboxymethyl)-1,4,7,10-tetraazacyclododecan-1-yl)methyl)isoquinoline 2-oxide (1);

1-((4-(2-amino-2-oxoethyl)-7,10-bis(carboxymethyl)-1,4,7,10-tetraazacyclododecan-1-yl)methyl)isoquinoline 2-oxide (2);

1-((4,10-bis(2-amino-2-oxoethyl)-7-(phosphonomethyl)-1,4,7,10-tetraazacyclododecan-1-yl)methyl)isoquinoline 2-oxide (3);

1,1'-((7,10-bis(carboxymethyl)-1,4,7,10-tetraazacyclododecane-1,4-diyl)bis(methylene))bis(isoquinoline 2-oxide) (4);

1-((1,7,10-tris(carboxymethyl)-1,4,7,10-tetraazacyclotridecan-4-yl)methyl)isoquinoline 2-oxide (5);

1-((4,7,10-tris(carboxymethyl)-1,4,7,10-tetraazacyclotridecan-1-yl)methyl)isoquinoline 2-oxide (6);

1-((4,8,11-tris(carboxymethyl)-1,4,8,11-tetraazacyclotetradecan-1-yl)methyl)isoquinoline 2-oxide (7);

2,2',2''-(11-((6-chloropyridin-2-yl)methyl)-1,4,8,11-tetraazacyclotetradecane-1,4,8-triyl)triacetic acid (8);

2,2',2''-(11-((6-methylpyridin-2-yl)methyl)-1,4,8,11-tetraazacyclotetradecane-1,4,8-triyl)triacetic acid (9);

1-((4,7-bis(carboxymethyl)-1,4,7-triazonan-1-yl)methyl)isoquinoline 2-oxide (10);

1-((5,9-bis(carboxymethyl)-1,5,9-triazacyclododecan-1-yl)methyl)isoquinoline 2-oxide (11);

1-((4,8,12-tris(carboxymethyl)-1,4,8,12-tetraazacyclopentadecan-1-yl)methyl)isoquinoline 2-oxide (12).

The object of the present invention is further a method of chromatographic separation of rare earth elements and/or s-, p- and d-block metals, selected from groups II.A, III.A, IV.A, V.A metals, transitional metals (preferably I.B, II.B and VIII.B group), from a mixture of at least two metal ions, at least one of them being a metal selected from Ce, Dy, Er, Eu, Gd, Ho, La, Lu, Nd, Pr, Pm, Sm, Sc, Tb, Tm, Yb, Y, alkaline earth metals, Al, Ga, In, Tl, Sn, Pb, Bi, transitional metals (preferably at least one of them being a metal selected from Ce, Dy, Er, Eu, Gd, Ho, La, Lu, Nd, Pr, Pm, Sm, Sc, Tb, Tm, Yb, Y, Ca, Fe, Co, Ni, Cu, Zn, Al, Pb, Bi), which comprises the following steps:

(a) providing a mixture of at least one metal ion selected from Ce, Dy, Er, Eu, Gd, Ho, La, Lu, Nd, Pr, Pm, Sm, Sc, Tb, Tm, Yb, Y, alkaline eartch metals, Al, Ga, In, Tl, Sn, Pb, Bi, transitional metals, and at least one further metal ion, wherein said further metal ion is selected from rare earth metal ions, transition metal ions, non-transition metal ions and actinide ions, (b) metal ions comprised in said mixture are subjected to reaction with at least one compound of general formula (I) as defined in any one of the preceding claims to form chelates;

(c) the chelates from step (b) are subjected to chromatographic separation, preferably, the stationary phase is selected from silica (SiO$_2$), alumina (Al$_2$O$_3$), titania (TiO$_2$), zirconia (ZrO$_2$) or (C$_1$-C$_{18}$)derivatized reversed phase (such as C$_1$-C$_{18}$, phenyl, pentafluorophenyl, C$_1$-C$_{18}$ alkyl-phenyl or polymer-based reversed phase or carbon), and, preferably, the mobile phase comprises one or more of the solvents selected from water, C$_1$-C$_4$ alcohol, acetonitrile, acetone, N,N-dimethylformamide, dimethylsulfoxide, tetrahydrofurane, aqueous ammonia, the mobile phase can eventually comprise one or more additives for pH adjustment, such as acids, bases or buffers; the additives for pH adjustment are known to the person skilled in the art;

whereas optionally step (c) can be performed at least twice in order to increase the purity of at least one separated metal chelate;

and, optionally, (d) at least one metal chelate obtained from the chromatographic separation is subjected to acidic decomplexation to afford a non-complexed metal ion.

Preferably, fractions/spots containing the separated metal chelate from step (c) are combined together; preferably, the combined fractions containing the metal chelate being separated are concentrated, e.g. by evaporation, before repetition of step (c).

In one preferred embodiment, the method of chromatographic separation according to the present invention is the method of chromatographic separation of rare earth elements from a mixture of at least two metal ions, at least one of them being a rare earth metal selected from Ce, Dy, Er, Eu, Gd, Ho, La, Lu, Nd, Pr, Pm, Sm, Sc, Tb, Tm, Yb and Y, using compounds of general formula (I) as defined above, and comprising the following steps:

(a) providing a mixture of at least one rare earth metal ion selected from Ce, Dy, Er, Eu, Gd, Ho, La, Lu, Nd, Pr, Pm, Sm, Sc, Tb, Tm, Yb and Y, and at least one further metal ion, wherein said further metal ion is selected from rare earth metal ions, transition metal ions, non-transition metal ions and actinide ions, (b) metal ions comprised in said mixture are subjected to reaction with at least one compound of general formula (I) as defined above to form chelates;

(c) the chelates from step (b) are subjected to chromatographic separation, such as column chromatography, thin layer chromatography or high-performance liquid chromatography (HPLC); preferably, the stationary phase is selected from silica (SiO$_2$), alumina (Al$_2$O$_3$), titania (TiO$_2$), zirconia (ZrO$_2$) or (C$_1$-C$_{18}$)derivatized reversed phase (such as C$_1$-C$_{18}$, phenyl, pentafluorophenyl, C$_1$-C$_{18}$ alkyl-phenyl or polymer-based reversed phase or carbon)

and, preferably, the mobile phase comprises one or more of the solvents selected from water, C$_1$-C$_4$ alcohol, acetonitrile, acetone, N,N-dimethylformamide, dimethylsulfoxide, tetrahydrofurane, aqueous ammonia, the mobile phase can eventually comprise one or more additives for pH adjustment, such as acids, bases or buffers; the additives for pH adjustment are known to the person skilled in the art;

whereas optionally step (c) can be performed at least twice in order to increase the purity of at least one separated metal chelate;

and, optionally, (d) at least one metal chelate obtained from the chromatographic separation is subjected to acidic decomplexation to afford a non-complexed rare earth metal ion.

Preferably, fractions/spots containing the separated metal chelate from step (c) are combined together; preferably, the combined fractions containing the metal chelate being separated are concentrated, e.g. by evaporation, before repetition of step (c).

The further metal ion mentioned in step (a) is selected from rare earth metal ions, transition metal ions, non-transition metal ions and actinide ions. The rare earth metals are Ce, Dy, Er, Eu, Gd, Ho, La, Lu, Nd, Pr, Pm, Sm, Sc, Tb, Tm, Yb and Y, transition metals are metals of the d-block of the periodic table (groups I.B to VIII.B), non-transition metals are metals from the main group elements (groups A) of the periodic table and actinides are actinium through lawrencium, chemical elements with atomic numbers from 89 to 103.

The acid used for decomplexation in step (d) is preferably selected from hydrofluoric, hydrochloric, hydrobromic, hydroiodic, sulfuric, nitric, peroxosulfuric, perchloric, methanesulfonic, trifluoromethanesulfonic, formic, acetic, trifluoroacetic acid or a mixture thereof.

Step (d) can be followed by a chromatography of the resulting mixture in order to purify the free rare earth metal ions from molecules of the compound of general formula (I) or its fragments resulting from acid decomplexation. The method of chromatographic separation takes place in solution, and it is a routine work of a person skilled in the art to find suitable conditions for such chromatographic purification.

In one preferred embodiment, the chromatography in step a) is high-performance liquid chromatography (HPLC) performed using a stationary reversed phase, preferably selected from $C_1$-$C_{18}$, phenyl, pentafluorophenyl, $C_1$-$C_{18}$ alkyl-phenyl or polymer-based reversed phases, and a mobile phase consisting of water and 0-40% (vol.) of a water-miscible organic solvent, selected from the group comprising methanol, ethanol, propanol, isopropanol, acetonitrile, acetone, N,N-dimethylformamide, dimethylsulfoxide, tetrahydrofurane, and, optionally, the mobile phase further containing up to 10% (w/w) of an ion-pairing additive consisting of a cationic part and an anionic part, wherein the cationic part is selected from the group comprising $H^+$, $Na^+$, $K^+$, $Rb^+$, $Cs^+$, $NH_{4+}$, $C_1$-$C_8$ tetraalkylammonium, and wherein the anionic part is selected from the group comprising $F^-$, $Cl^-$, $Br^-$, $I^-$, sulfate, hydrogen sulfate, nitrate, perchlorate, methanesulfonate, trifluoromethanesulfonate, ($C_2$-$C_{18}$ alkyl)sulfonate, formate, acetate, ($C_2$-$C_{18}$ alkyl)carboxylate, lactate, malate, citrate, 2-hydroxyisobutyrate, mandelate, diglycolate, tartarate.

In a preferred embodiment, a solution containing the mixture provided in step (a) in the form of salts (e.g. chloride, bromide, sulfate, nitrate, methanesulfonate, trifluoromethanesulfonate, formate, acetate, lactate, malate, citrate, 2-hydroxyisobutyrate, mandelate, diglycolate, tartarate) or a solid phase containing the mixture provided in step (a) (e.g. in the form of oxide, hydroxide, carbonate), is mixed with a solution of the compound of general formula (I) in molar ratio of metal ions to compound of general formula (I) from 1:0.5 to 1:100, preferably from 1:0.7 to 1:50, more preferably from 1:0.9 to 1:10. Concentrations of the soluble components may be selected from the concentration range permitted by solubility of such compounds in a given solvent at a given temperature, preferably in the concentration range 0.000001-0.5 mol/L. The solvent may be water, a water-miscible organic solvent such as methanol, ethanol, propanol, isopropanol, acetone, acetonitrile, N,N-dimethylformamide, dimethylsulfoxide, tetrahydrofurane, or a mixture thereof. An organic or inorganic base, such as LiOH, NaOH, KOH, aqueous $NH_3$, triethylamine, N,N-diisopropylethylamine or pyridine, is added to the reaction mixture in order to compensate for protons released during the complexation, and the complexation takes place in the solution. Preferably, 1-10 molar equivalents of base are added per molecule of the compound of general formula (I). Eventually, the reaction can take place in a buffer. In such case there is no need of adding organic or inorganic base to the reaction mixture. The mixture is stirred or shaken at room temperature or elevated temperature for up to 24 hours to afford complete complexation. Preferably, the mixture is stirred or shaken at 40° C. for 15 minutes. A reasonable excess of the compound of general formula (I) may be used to accelerate the complexation and to shift the equilibrium towards formation of the chelates. The result of step (b) is a mixture of different metal chelates in solution.

In a preferred embodiment, the chromatographic separation of the chelates in step (b) takes place on normal or reversed stationary phase. The normal phase may be silica ($SiO_2$) or alumina ($Al_2O_3$). A variety of reversed phases may be used, including $C_1$-$C_{18}$, phenyl, pentafluorophenyl, ($C_1$-$C_{18}$ alkyl)-phenyl and polymer-based reversed phases. The solution of metal chelates may optionally be centrifuged or filtered prior to the chromatography in step (b), in order to remove particulates, such as insoluble impurities or dust. The separation may be achieved via a variety of chromatographic arrangements including column chromatography, thin layer chromatography (TLC) and high-performance liquid chromatography (HPLC). The excess of compound of general formula (I) is also separated during the chromatography. Preferably, the chromatographic separation is achieved using HPLC on $C_8$, $C_{18}$ or phenyl-hexyl reversed phase. In a preferred embodiment, a mobile phase is used that consists of water and 3-40% of methanol, ethanol or acetonitrile. Optionally, 0.01-0.1 mol/L of a buffer is used in the mobile phase, wherein the buffer comprises sodium acetate pH=4.5, ammonium formate pH=7.0 or ammonium acetate pH=7.0. Fractions containing the desired metal chelate are collected and combined, resulting in a solution significantly enriched in the content of the desired rare earth metal chelate compared to the original mixture of metal chelates prior to the chromatography. The process may be repeated to further increase the purity of the product.

In a preferred embodiment, the decomposition of the purified chelate in step (d) is performed by treating of the solution of the chromatographically purified chelate with an organic or inorganic acid in order to achieve decomplexation of the metal ion from the chelate. The organic or inorganic acid is selected from a group comprising hydrofluoric, hydrochloric, hydrobromic, hydroiodic, sulfuric, nitric, peroxosulfuric, perchloric, methanesulfonic, trifluoromethanesulfonic, formic, acetic, trifluoroacetic acid or a mixture thereof. The choice of the acid and of reaction conditions for achieving completeness of the decomplexation would be apparent to a person skilled in the art. Preferably, the decomplexation is achieved by using hydrochloric acid (0.01-12 mol/L) at 25-95° C. for time period of 5 minutes to 24 hours. A secondary chromatographic purification is then performed to remove the free chelator molecule (compound of general formula (I)) from rare earth metal ions. This may be achieved by a column chromatography or solid-phase extraction using a stationary reversed phase. Preferably, the reversed phase is $C_{18}$ or polymer-based reversed phase. Preferably, a mobile phase is used that consists of pure water or water containing 0.01-1% (vol.) of the acid used in step (d) for decomposition of the chelate. The chelator is retained on the reversed phase, while the free metal ions are eluted in the form of a salt with the acid used in step (d) for decomposition of the chelate. Alternatively, the chromatographic separation described in step (c) is used. Yet another alternative is mineralization of the purified metal chelate by means of oxidation in nitric acid or peroxosulfuric acid. Preferably, the mineralization is achieved by mixing 1 part of the metal chelate solution with 4 or more parts of 70% nitric acid and incubating at 25-95° C. for time period of 5 minutes to 24 hours. In such case the chelator molecule is digested and no separation is needed.

The increase of concentration of combined fractions containing the metal chelate being separated before repetition of step (c) can be achieved by partial evaporation of the solvent or by adsorption of the chelate to lipophilic materials, such as a reversed phase. Preferably, the same reversed phase is used as for the chromatographic separation in step (c). When aqueous solution of the chelate is brought to physical contact with the reversed phase, it results in adsorption of the chelate. The chelate may then be desorbed from the reversed phase with a stronger eluent, wherein the stronger eluent contains higher percentage of a water-miscible organic solvent than the original solution of the chelate, wherein the water-miscible organic solvent is methanol, ethanol, propanol, isopropanol, acetone, acetonitrile, N,N-dimethylformamide, dimethylsulfoxide, tetrahydrofurane, or a mixture thereof. The strength of the eluent is controlled by the percentage of the water-miscible organic solvent in the mobile phase.

In a preferred embodiment, solution of metal chelates of the compounds of general formula (I) are concentrated by adsorption to reversed phase in two steps: (i) A diluted aqueous solution of the chelate is passed through the reversed phase, resulting in adsorption of the chelate. If the solution is a chromatographic fraction collected from a previous chromatographic separation and, as such, contains a water-miscible organic solvent, it is first diluted with distilled water prior to adsorption to decrease the eluent strength. Preferably, the solution is diluted with equal or higher volume of water, thus decreasing the percentage of the water-miscible organic solvent to one half or less of the original value. (ii) In the second step, the chelate is desorbed from the reversed phase with a stronger eluent containing higher percentage of the water-miscible organic solvent. Preferably, the mobile phase used for chromatographic separation in step (c) is used as the eluent. In that case, a secondary chromatographic separation can be directly performed. Alternatively, a stronger eluent is used of a volume that is smaller than the original volume of adsorbed solution and the desorbed metal chelate is directly collected. In that case the concentration of the metal chelate is increased compared to the original solution. The advantage of this method is that it allows concentrating solutions of metal chelates without the need for time consuming evaporation, an operation that is not preferred particularly when working with radionuclides. Importantly, on a reversed-phase chromatographic column this method leads to sorption of the metal chelates in a narrow band at the beginning of the column and consecutively leads to sharp peaks and more efficient chromatographic separation. This is in contrast to broad peaks and poor separation that would result from the presence of a strong eluent in previously collected fractions, if such fractions were used unchanged for another chromatographic separation. Moreover, this method allows to repeat the chromatographic separations of previously collected chromatographic fractions in fast succession. Fast repetition of the chromatographic purification provides the desired metal chelate in high purity in shorter time.

The object of the present invention are also compounds of general formula (Ia), (Ia)

wherein

X is selected from a group consisting of H; $C_1$ to $C_6$ alkyl; halogen (F, Cl, Br or I); preferably X is selected from a group consisting of H; —$CH_3$; halogen;

Y is selected from a group consisting of nitrogen; N-oxide;

$Z^1$, $Z^2$, $Z^m$, wherein m is 1 or 2, are independently selected from the group consisting of —$CH_2$—$CH_2$— and —$CH_2$—$CH_2$—$CH_2$—;

A, $A^m$, wherein m is 1 or 2, are independently selected from H; —$CH_2COOH$; —$CH_2C(O)NH_2$; —$CH_2P(O)(OH)_2$; and wherein at most one of A, $A^m$ is H;

n is 1 or 2;

$R^1$, $R^2$, $R^3$ are independently H; $C_1$ to $C_6$ alkyl; $C_1$ to $C_6$ alkyloxy; $C_6$ to $C_{10}$ aryloxy; benzyloxy; $C_1$ to $C_6$ alkylthio; $C_6$ to $C_{10}$ arylthio; F; Cl; Br; I; OH; SH; $NH_2$; $C_1$ to $C_6$ alkylamino; di($C_1$ to $C_6$ alkyl)amino; $C_1$ to $C_6$ acylamino; di($C_1$ to $C_6$ acyl)amino; $C_6$ to $C_{10}$ acylamino; di($C_6$ to $C_{10}$ aryl)amino; CN; OH; nitro; $COOR_n$, $C(O)NHR_n$, $C(O)N(R_n)_2$, wherein $R_n$ is independently H or $C_1$ to $C_{10}$ alkyl or $C_6$ to $C_{10}$ aryl;

and/or neighboring two of $R^1$, $R^2$, $R^3$ together with neighboring two carbon atoms of the aromatic cycle form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl)amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl;

with the proviso that:

when n is 2, all of $Z^1$, $Z^2$, $Z^m$ are —$CH_2$—$CH_2$—, then A is not —$CH_2COOH$;

when Y is nitrogen, then X is not H;

when n is 1, all of $Z^1$, $Z^2$, $Z^m$ are —$CH_2$—$CH_2$—, and Y is nitrogen, then X is not halogen.

The general formula (Ia) of the present invention is meant to include all isomers, enantiomers and diastereoisomers.

In one preferred embodiment of the compounds of general formula (Ia) according to the present invention, X is selected from a group consisting of H; —CH$_3$ and Cl.

In one preferred embodiment of the compounds of general formula (Ia) according to the present invention, R$^1$, R$^2$, R$^3$ are independently H; C$_1$ to C$_6$ alkyl; and/or neighboring two of R$^1$, R$^2$, R$^3$ together with neighboring two carbon atoms of the aromatic cycle form a six-membered ring, optionally substituted with one or more substituents independently selected from the group consisting of OH, SH, CF$_3$, F, Cl, Br, I, C$_1$ to C$_6$ alkyl, C$_1$ to C$_6$ alkyloxy, C$_1$ to C$_6$ alkylthio, NH$_2$, C$_1$ to C$_6$ alkylamino, di(C$_1$ to C$_6$ alkyl)amino, NO$_2$, COOH, COOR$_n$, C(O)NHR$_n$, C(O)N(R$_n$)$_2$, wherein R$_n$ is independently H or C$_1$ to C$_{10}$ alkyl or C$_6$ to C$_{10}$ aryl.

In one preferred embodiment of the compounds of general formula (Ia) according to the present invention, at least two of A, A''' are —CH$_2$COOH and/or —CH$_2$P(O)(OH)$_2$.

In one preferred embodiment of the compounds of general formula (Ia) according to the present invention, at most one of A, A''' is H.

In one preferred embodiment of the compounds of general formula (Ia) according to the present invention, X is —CH$_3$ or Cl, Y is nitrogen, and all of R$^1$, R$^2$, R$^3$ are H.

In another preferred embodiment of the compounds of general formula (la) according to the present invention, X is H, Y is N-oxide, and two of R$^1$, R$^2$, R$^3$ together with neighboring two carbon atoms of the aromatic cycle form a six-membered ring, optionally substituted with one or more substituents independently selected from the group consisting of OH, SH, CF$_3$, F, Cl, Br, I, C$_1$ to C$_6$ alkyl, C$_1$ to C$_6$ alkyloxy, C$_1$ to C$_6$ alkylthio, NH$_2$, C$_1$ to C$_6$ alkylamino, di(C$_1$ to C$_6$ alkyl)amino, NO$_2$, COOH, COOR$_n$, C(O)NHR$_n$, C(O)N(R$_n$)$_2$, wherein R$_n$ is independently H or C$_1$ to C$_{10}$ alkyl or C$_6$ to C$_{10}$ aryl.

In one preferred embodiment of the compounds of general formula (Ia) according to the present invention, R$^1$, R$^2$, R$^3$ are independently selected from H, OH, OCH$_3$, NO$_2$, F, Cl, Br, I, CH$_3$, COOH, COOR$_n$, C(O)NHR$_n$, C(O)N(R$_n$)$_2$, wherein R$_n$ is defined as above.

Preferably, the ring containing Y atom is selected from isoquinoline N-oxide, quinoline N-oxide, isoquinoline, quinoline, pyridine, pyridine N-oxide; more preferably, the ring containing Y atom is a pyridine ring, quinoline N-oxide or isoquinoline N-oxide.

In one preferred embodiment of the compounds of general formula (Ia) according to the present invention, compounds of general formula (I) are selected from the group consisting of: 1-((4,7-bis(carboxymethyl)-1,4,7,10-tetraazacyclododecan-1-yl)methyl)isoquinoline 2-oxide (1);

1-((4-(2-amino-2-oxoethyl)-7,10-bis(carboxymethyl)-1,4,7,10-tetraazacyclododecan-1-yl)methyl)isoquinoline 2-oxide (2);

1-((4,10-bis(2-amino-2-oxoethyl)-7-(phosphonomethyl)-1,4,7,10-tetraazacyclododecan-1-yl)methyl)isoquinoline 2-oxide (3);

1-((1,7,10-tris(carboxymethyl)-1,4,7,10-tetraazacyclotridecan-4-yl)methyl)isoquinoline 2-oxide (5);

1-((4,7,10-tris(carboxymethyl)-1,4,7,10-tetraazacyclotridecan-1-yl)methyl)isoquinoline 2-oxide (6);

1-((4,8,11-tris(carboxymethyl)-1,4,8,11-tetraazacyclotetradecan-1-yl)methyl)isoquinoline 2-oxide (7);

2,2',2''-(11-((6-chloropyridin-2-yl)methyl)-1,4,8,11-tetraazacyclotetradecane-1,4,8-triyl)triacetic acid (8);

2,2',2''-(11-((6-methylpyridin-2-yl)methyl)-1,4,8,11-tetraazacyclotetradecane-1,4,8-triyl)triacetic acid (9);

1((4,7-bis(carboxymethyl)-1,4,7-triazonan-1-yl)methyl)isoquinoline 2-oxide (10);

1-((5,9-bis(carboxymethyl)-1,5,9-triazacyclododecan-1-yl)methyl)isoquinoline 2-oxide (11);

1-((4,8,12-tris(carboxymethyl)-1,4,8,12-tetraazacyclopentadecan-1-yl)methyl)isoquinoline 2-oxide (12).

The disclosed invention represents an integrated approach for manipulation with metal ions in solution that greatly simplifies their transfer, purification and volume reduction, while simultaneously preventing contamination with other metals. This is particularly useful in handling metal radionuclides where these operations are problematic. The present invention allows performing these operations in rapid succession, repeatedly and in varying order.

The method for chromatographic separation of metal ions according to the present invention is distinctly different from the existing chromatographic methods. In the existing methods, the selectivity towards different elements, such as rare earth elements, is introduced by the stationary phase, or by an additive that is added to the mobile phase in excess relative to the separated metals, or by both simultaneously (Kifle, D., Wibetoe, G. (2013), *J. Chromatogr. A* 1307, 86-90; Schwantes, J. M. et al. (2008) *J. Radioanal. Nucl. Chem.* 276(2), 533-542). In contrast, in the method according to the present invention the selectivity originates from the chelator molecule that remains closely associates with the metal ion throughout the whole separation process. The present invention thus allows using conventional stationary phases (e.g. normal phase: SiO$_2$, reversed phase: C$_{18}$, C$_8$, phenyl-hexyl, phenyl, polymer-based reversed phase) and mobile phases (such as: water/acetonitrile, water/methanol, water/ethanol, water/isopropanol), bearing no particular selectivity towards the particular elements for their efficient separation.

There are several distinct features of the chelators disclosed in this invention that present an important difference from the chelators and ligands used in the existing techniques for separation of elements, such as rare earth elements. The disclosed chelators possess an aromatic moiety that plays a major role in the polarity of the metal chelates. For this reason, the aromatic moiety is crucial for the ability of the chelators to distinguish metals based on polarity of the chelates. In addition, the aromatic moiety serves as a chromophore that facilitates detection of the chelator and metal chelates based on UV absorbance or quenching of fluorescence on a TLC plate. Another important feature of the disclosed chelators is that they form chelates with metals that are kinetically inert for the duration of the separation process. Notably, this property reduces the risk of contamination with other metals, as the metal to be purified cannot readily escape from the chelate nor can it be replaced by another metal ion.

The present invention provides a fast and convenient way to efficient separation even of neighboring lanthanides from each other, i.e. a separation that is a notoriously difficult problem.

All these operations can be easily automated to limit exposure of the operator to radiation in case that metal radionuclides are used. Presence of an aromatic chromophore moiety in the structure of the chelators facilitates detection by UV absorbance or by quenching of fluorescence on a TLC plate. Therefore, the present invention represents an integrated approach allowing to perform rapid transfer, purification and volume reduction of solutions of metal radionuclides.

EXAMPLES

The numerical values of chemical shift in NMR spectra are given in ppm. Notation used in the NMR spectra: s (singlet), d (dublet), t (triplet), m (multiplet), bs (broad singlet). The reference was set to the following values:

$^1$H (25° C.): 7.26 ppm (CDCl$_3$); 3.75 ppm (Dioxane); 4.70 ppm (HOD).

$^1$H (90° C.): 3.75 ppm (Dioxane); 4.23 ppm (HOD).

$^{13}$C (90° C.): 67.2 ppm (Dioxane).

$^{13}$C (25° C.): 77.16 ppm (CDCl$_3$); 66.6 ppm (Dioxane).

$^{31}$P (25° C.): 0.0 ppm (H$_3$PO$_4$).

LIST OF ABBREVIATIONS

ESI (electrospray ionization); HPLC (high performance liquid chromatography); HRMS (high resolution mass spectrometry); LC-MS (liquid chromatography-mass spectrometry); MOPS (3-morpholinopropane-1-sulfonic acid); NCA (no-carrier-added); TFA (trifluoroacetic acid); TLC (thin layer chromatography); UV (ultraviolet).

I. Synthesis of Compounds

Structures of starting macrocyclic derivatives A, B, C, D, E and F

A

B

Example 1: Preparation of 1-(bromomethyl)isoquinoline 2-oxide (1a)

1-(bromomethyl)isoquinoline (150 mg, 0.675 mmol) was dissolved in chloroform (15 mL) and cooled in water-ice bath. m-chloroperoxobenzoic acid (77%, 0.230 g, 1.03 mmol) was added while stirring. The reaction mixture was let to gradually warm up to room temperature and stirred for 24 hours. The solvent was evaporated and the residue was purified by column chromatography on silica in methanol/ethyl acetate mixture. Fractions containing the product were evaporated to give 102 mg of product as pale yellow solid (0.430 mmol, 64% yield relative to 1-(bromomethyl)isoquinoline).

$^1$H NMR (CDCl$_3$, 25° C., 500 MHz): δ$_H$ 5.17 (CH$_2$-arom., s, 2H); 7.61 (arom., ddd, 1H, $^3$J$_{HH}$=8 Hz, $^3$J$_{HH}$=7 Hz, $^4$J$_{HH}$=1 Hz); 7.64 (arom., d, 1H, $^3$J$_{HH}$=7 Hz); 7.73 (arom., ddd, 1H, $^3$J$_{HH}$=9 Hz, $^3$J$_{HH}$=7 Hz, $^4$J$_{HH}$=1 Hz); 7.80-7.83 (arom., m, 1H); 7.95 (arom., ddd, 1H, J$_{HH}$=9 Hz, $^4$J$_{HH}$=2 Hz, $^4$J$_{HH}$=1 Hz); 8.19 (arom., d, 1H, $^3$J$_{HH}$=7 Hz); $^{13}$C{$^1$H} NMR (CDCl$_3$, 25° C., 125 MHz): δ$_C$ 20.9 (CH$_2$-arom., s); 122.9 (arom., s); 124.0 (arom., s); 127.6

(arom., s); 127.8 (arom., s); 128.6 (arom., s); 128.8 (arom., s); 129.9 (arom., s); 136.9 (arom., s); 143.1 (arom., s).

HRMS (ESI) m/z: [(M+H)$^+$] ($C_{10}H_9BrNO$) calculated: 237.9862, found: 237.9863.

Preparation of 14(4,7-bis(carboxymethyl)-1,4,7,10-tetraazacyclododecan-1-yl)methypisoquinoline 2-oxide (1)

Starting compound A (145 mg, 0.362 mmol), 1-(bromomethyl)isoquinoline 2-oxide (86 mg, 0.362 mmol) and cesium carbonate (354 mg, 1.09 mmol) were dissolved in acetonitrile (10 mL) and stirred for 24 hours at room temperature. The solids were filtered off and the filtrate was concentrated on rotary evaporator. Resulting oil was purified on preparative HPLC ($C_{18}$ column, acetonitrile/water gradient with 0.1% TFA in the mobile phase). At this point, the doubly alkylated byproduct was also collected and processed separately. Fractions containing pure product in the form of tert.butyl ester were pooled, evaporated and dried in high vacuum. The resulting oil was divided into two equal parts that were processed separately. One part was used for further synthesis as described in Example 2. The second part was dissolved in neat TFA (4 mL) and stirred for 24 h at room temperature. TFA was evaporated on rotary evaporator, the residue dissolved in distilled water (2 mL) and purified on preparative HPLC (same conditions as above). Fractions containing the product were pooled and evaporated. The residue was dissolved in distilled water (2 mL) and lyophilized, giving 41.0 mg of the product as a white fluffy solid (0.055 mmol, 30% yield relative to A).

$^1$H NMR (D$_2$O with internal dioxane reference, 25° C., 500 MHz): δ$_H$ 2.64-3.95 (8×cycle CH$_2$+2×CH$_2$—COOH, 20H); 4.13-4.39 (CH$_2$-arom., m, 2H); 7.64-7.78 (2×arom., m, 2H); 7.82-7.93 (2×arom., m, 2H); 8.09 (arom., d, 1H, $^3J_{HH}$=7 Hz); 8.14 (arom., d, 1H, $^3J_{HH}$=8 Hz). $^{13}$C{$^1$H} NMR (D$_2$O with internal dioxane reference, 25° C., 125 MHz): 42.5 (CH$_2$—COOH, s); 42.6 (CH$_2$—COOH, s); 45.3 (cycle, s); 47.1 (CH$_2$-arom., s); 48.1 (cycle, s); 49.1 (cycle, s); 50.1 (cycle, s); 50.9 (cycle, s); 52.8 (cycle, s); 53.1 (cycle, s); 53.2 (cycle, s); 123.5 (arom., s); 125.4 (arom., s); 127.7 (arom., s); 128.1 (arom., s); 130.6 (arom., s); 130.9 (arom., s); 131.0 (arom., s); 135.8 (arom., s); 144.0 (arom., s); 166.7 (CO, s); 173.5 (CO, s).

HRMS (ESI) m/z: [(M+H)$^+$] ($C_{22}H_{32}N_5O_5$) calculated: 446.2398, found: 446.2397.

Elem. analysis: M·2.3TFA·2.2H$_2$O, calculated: C (42.7), H (5.1), N (9.4), F (17.5), found: C (42.8), H (4.5), N (8.9), F (17.4).

Example 2: 1-((4-(2-amino-2-oxoethyl)-7,10-bis(carboxymethyl)-1,4,7,10-tetraazacyclododecan-1-yl)methypisoquinoline 2-oxide (2)

The synthesis started from compounds A and 1-(bromomethyl)isoquinoline 2-oxide as described in Example 1 up to the stage where the intermediate bis(tert.butyl) ester of compound 1, (t-Bu$_2$1), was obtained by preparative HPLC. A solution of t-Bu$_2$1 (estimated 57 mg, 0.102 mmol, ½ of the total prepared in Example 1) as obtained from preparative HPLC was neutralized with cesium carbonate to pH=7, evaporated and dried in high vacuum. The resulting solid was dissolved in acetonitrile (10 mL), cesium carbonate was added (110 mg, 0.338 mmol), followed by addition of iodoacetamide (48.4 mg, 0.262 mmol). The suspension was stirred for 48 h at 80° C. The solids were filtered off and the filtrate was concentrated on rotary evaporator. Resulting oil was purified on preparative HPLC ($C_{18}$ column, acetonitrile/water gradient with 0.1% TFA in the mobile phase). Fractions containing pure product in the form of tert.butyl ester were pooled, evaporated and dried in high vacuum. The residue was dissolved in neat TFA (4 mL) and stirred for 24 h at room temperature. TFA was evaporated on rotary evaporator, the residue dissolved in distilled water (2 mL) and purified on preparative HPLC (same conditions as above). Fractions containing the product were pooled and evaporated. The residue was dissolved in distilled water (2 mL) and lyophilized, giving 33.4 mg of the product as a white fluffy solid (0.041 mmol, 33% yield relative to A).

$^1$H NMR (D$_2$O with internal dioxane reference, 90° C., 500 MHz): Eu 3.40-4.05 (8×cycle CH$_2$+CH$_2$—COOH+CH$_2$—CONH$_2$, 20H); 4.40 (CH$_2$—COOH, s, 2H); 5.42 (CH$_2$—arom., s, 2H); 8.23-8.34 (2×arom., m, 2H); 8.45-8.50 (arom., m, 1H); 8.52 (arom., d, 1H, $^3J_{HH}$=7 Hz); 8.58-8.64 (arom., m, 1H); 8.64 (arom., d, 1H, $^3J_{HH}$=7 Hz). $^{13}$C{$^1$H} NMR (D$_2$O with internal dioxane reference, 90° C., 125 MHz): 49.1 (cycle, s); 49.8 (cycle, s); 49.9 (cycle, s); 50.1 (cycle, s); 50.5 (CH$_2$-arom., s); 51.6 (cycle, s); 51.6 (cycle, s); 51.8 (cycle, s); 51.8 (cycle, s); 53.3 (CH$_2$—COOH, s); 54.4 (CH$_2$—CONH$_2$, s); 55.2 (CH$_2$—COOH, s); 123.5 (arom., s); 127.4 (arom., s); 128.9 (arom., s); 129.0 (arom., s); 131.4 (arom., s); 131.6 (arom., s); 132.1 (arom., s); 135.8 (arom., s); 139.2 (arom., s); 170.2 (CO, s); 172.3 (CO, s); 172.4 (CO, s).

HRMS (ESI) m/z: [(M+H)$^+$] ($C_{24}H_{35}N_6O_6$) calculated: 503.2613, found: 503.2611.

Elem. analysis: M·2.5TFA·1.6H$_2$O, calculated: C (42.7), H (4.9), N (10.3), F (17.5), found: C (42.9), H (4.5), N (9.6), F (17.1).

Example 3: 14(4,10-bis(2-amino-2-oxoethyl)-7-(phosphonomethyl)-1,4,7,10-tetraazacyclododecan-1-yl)methyl)isoquinoline 2-oxide (3)

Cyclen (300 mg, 1.74 mmol) and paraformaldehyde (78.4 mg, 2.61 mmol) were mixed under argon atmosphere and dissolved in dry tetrahydrofuran (12 mL). tri(tert.butyl) phosphite (654 mg, 2.61 mmol) was added and the mixture was stirred at room temperature under argon for 24 h. The solvent was evaporated on rotary evaporator, the residue purified on preparative HPLC ($C_{18}$ column, acetonitrile/water gradient with 0.1% TFA in the mobile phase). Mass spectrometer was used for detection. The intermediate with single phosphonate arm, i.e. di-tert-butyl ((1,4,7,10-tetraazacyclododecan-1-yl)methyl)phosphonate, was collected based on mass (m/z for $[M+H]^+$=379).

Fraction containing this intermediate were pooled, neutralized with cesium carbonate to pH=7, evaporated on rotary evaporator and dried in high vacuum. The resulting solid was mixed with cesium carbonate (400 mg, 1.84 mmol), acetonitrile (10 mL) and stirred for 30 minutes at room temperature. Then, 1-(bromomethyl)isoquinoline 2-oxide (55.3 mg, 0.232 mmol) was added and the mixture was stirred 6 h at 80° C. The solids were filtered off, the solvent was evaporated on rotary evaporator and the residue was purified on preparative HPLC (same as above). Major peak corresponding to mono-alkylated intermediate (m/z for $[M+H]^+$=536) was collected. Fraction containing this intermediate were pooled, neutralized with cesium carbonate to pH=7, evaporated on rotary evaporator and dried in high vacuum. The resulting solid was mixed with cesium carbonate (73 mg, 0.224 mmol), acetonitrile (4 mL) and iodoacetamide (10.4 mg, 0.056 mmol) and stirred at room temperature for 3 h. The solids were filtered off, the solvent was evaporated on rotary evaporator and the residue was purified on preparative HPLC (same as above). Fractions containing the product in the form of tert.butyl ester were pooled and the solvent was evaporated on rotary evaporator. The residue was dissolved in 2 mL of TFA and stirred for 24 h. TFA was evaporated on rotary evaporator, the residue dissolved in distilled water (2 mL) and purified on preparative HPLC (same conditions as above). Fractions containing the product were pooled and evaporated. The residue was dissolved in distilled water (2 mL) and lyophilized, giving 10.3 mg of the product as a white fluffy solid (yield not determined).

$^1$H NMR (D$_2$O with internal dioxane reference, 90° C., 500 MHz): $\delta_H$ 3.03-4.08 (8×cycle CH$_2$+2×CH$_2$—CONH$_2$, 20H); 4.26 (CH$_2$—PO$_3$H$_2$, bs, 2H); 5.03 (CH$_2$—arom., bs, 2H); 8.23-8.36 (2×arom., m, 2H); 8.45-8.52 (2×arom., m, 2H); 8.60-8.65 (arom., m, 1H); 8.70 (arom., d, 1H, $^3J_{HH}$=8 Hz). $^{31}$P{$^1$H} NMR (D$_2$O with external H$_3$PO$_4$ reference, 25° C., 202 MHz): $\delta_P$ 9.6 ppm (bs).

HRMS (ESI) m/z: $[(M+H)^+]$ ($C_{23}H_{37}N_7O_6P$) calculated: 538.2537, found: 538.2531.

Example 4: 1,1'-((7,10-bis(carboxymethyl)-1,4,7,10-tetraazacyclododecane-1,4-diyl)bis(methylene))bis(isoquinoline 2-oxide) (4)

The compound was synthesized according to the procedure in Example 1 as the doubly alkylated byproduct, giving analogously 56.7 mg of the product as a white fluffy solid (0.061 mmol, 17% yield relative to A).

$^1$H NMR (D$_2$O with internal dioxane reference, 25° C., 500 MHz): 6H 2.80-3.93 (8×cycle CH$_2$+2×CH$_2$—COOH, 20H); 4.71 (CH$_2$-arom., s, 4H); 7.56-7.72 (2×arom., m, 4H); 7.78-7.84 (arom., m, 2H); 7.84-7.90 (arom., m, 2H); 7.98-8.04 (arom., m, 2H); 8.04-8.10 (arom., m, 2H). $^{13}$C{$^1$H} NMR (D$_2$O with internal dioxane reference, 25° C., 125 MHz): 48.2 (CH$_2$-arom., s); 49.8 (cycle, bs); 50.0 (cycle, bs); 50.2 (cycle, bs); 50.3 (cycle, bs); 53.2 (CH$_2$—COOH, s); 123.1 (arom., s); 126.3 (arom., s); 128.0 (arom., s); 128.5 (arom., s); 130.6 (arom., s); 130.6 (arom., s); 130.9 (arom., s); 135.1 (arom., s); 141.1 (arom., s); 172.4 (CO, s).

HRMS (ESI) m/z: $[(M+H)^+]$ ($C_{32}H_{39}N_6O_6$) calculated: 603.2926, found: 603.2924.

Elem. analysis: M·2.6TFA·1.4H$_2$O, calculated: C (48.3), H (4.7), N (9.1), F (16.0), found: C (48.4), H (4.6), N (9.0), F (15.9).

Example 5: 1-((1,7,10-tris(carboxymethyl)-1,4,7,10-tetraazacyclotridecan-4-yl)methyl)isoquinoline 2-oxide (5)

Starting compound C (42.7 mg, 0.229 mmol) was dissolved in a mixture of acetonitrile (3 mL) and dimethylformamide (0.5 mL). Then, 1-(bromomethyl)isoquinoline 2-oxide (40 mg, 0.168 mmol) was added and the mixture was stirred at room temperature for 24 h. The mixture was concentrated on rotary evaporator and the residue was purified on preparative HPLC ($C_{18}$ column, acetonitrile/water gradient with 0.1% TFA in the mobile phase). Two isomers of mono-alkylated intermediate (m/z for $[M+H]^{30}$=344) were successfully separated and processed separately. Fractions containing the earlier-eluting of the two were pooled, evaporated on rotary evaporator and dried in high vacuum. The residue was dissolved in acetonitrile (1 mL), cesium carbonate (84.7 mg, 0.260 mmol) was added and the mixture was stirred for 10 min at room temperature. Then, tert.butyl bromoacetate (29.6 mg, 0.152 mmol) was added and the mixture was stirred at room temperature for 24 h. The solids were filtered off and the filtrate was concentrated on rotary evaporator. Resulting oil was purified on preparative HPLC ($C_{18}$ column, acetonitrile/water gradient with 0.1% TFA in the mobile phase). Fractions containing the product in the form of tert.butyl ester were pooled, evaporated on rotary evaporator and dried in high vacuum. The residue was dissolved in neat TFA (2 mL) and the mixture was stirred for 24 h at room temperature. TFA was evaporated on rotary evaporator, the residue dissolved in distilled water (2 mL) and purified on preparative HPLC (same conditions as above). Fractions containing the product were pooled and evaporated. The residue was dissolved in distilled water (2 mL) and lyophilized, giving 8 mg of the product as a white fluffy solid (0.011 mmol, 7% yield relative to 1-(bromomethyl)isoquinoline 2-oxide).

$^1$H NMR ($D_2O$ with internal dioxane reference, 25° C., 500 MHz): $\delta_H$ 2.01 ($CH_2$—$CH_2$—$CH_2$, m, 2H); 2.79-3.70 (8×cycle $CH_2$+2×$CH_2$—COOH, 20H); 3.97 ($CH_2$—COOH, s, 2H); 5.03 ($CH_2$—arom., s, 2H);

7.80-7.92 (2×arom., m, 2H); 8.03-8.08 (arom., m, 1H); 8.14 (arom., d, 1H, $^3J_{HH}$=7 Hz); 8.20-8.26 (arom., m, 1H); 8.35 (arom., d, 1H, $^3J_{HH}$=7 Hz). $^{13}C\{^1H\}$ NMR ($D_2O$ with internal dioxane reference, 25° C., 125 MHz): 21.9 ($CH_2$—$CH_2$—$CH_2$, s); 49.6 (cycle, s); 49.9 (cycle, bs); 50.3 (cycle, s); 50.4 ($CH_2$-arom., s); 50.6 (cycle, s); 50.9 (cycle, s); 51.6 (cycle, s); 52.8 (cycle, s); 53.7 ($CH_2$—COOH, s); 53.9 (cycle, s); 54.8 ($CH_2$—COOH, bs); 55.0 ($CH_2$—COOH, s); 123.3 (arom., s); 127.2 (arom., s); 128.3 (arom., s); 128.5 (arom., s); 131.4 (arom., s); 131.5 (arom., s); 131.5 (arom., s); 135.1 (arom., s); 139.2 (arom., s); 169.8 (CO, s); 172.8 (CO, s); 172.9 (CO, s).

HRMS (ESI) m/z: [(M+H)$^+$] ($C_{25}H_{36}N_5O_7$) calculated: 518.2609, found: 518.2604.

Elem. analysis: M·1.5TFA·2.8$H_2O$, calculated: C (45.5), H (5.7), N (9.5), F (11.6), found: C (45.7), H (5.1), N (9.2), F (11.1).

Example 6: 14(4,7,10-tris(carboxymethyl)-1,4,7,10-tetraazacyclotridecan-1-yl)methyl)isoquinoline 2-oxide (6)

The compound was prepared following the procedure in Example 5 as the second isomer. Analogously, using cesium carbonate (80.1 mg, 0.246 mmol) and tert.butyl bromoacetate (28 mg, 0.143 mmol) in the second step and following the same procedure, 7 mg of final product was obtained as a white fluffy solid (0.0094 mmol, 6% yield relative to 1-(bromomethyl)isoquinoline 2-oxide).

$^1$H NMR ($D_2O$ with internal dioxane reference, 25° C., 500 MHz): $\delta_H$ 2.06-2.18 ($CH_2$—$CH_2$—$CH_2$, m, 2H); 2.87-3.35 (6×cycle $CH_2$, 12H); 3.39-3.64 (2×cycle $CH_2$+2×$CH_2$—COOH, 8H); 3.93 ($CH_2$—COOH, s, 2H); 5.02 ($CH_2$—arom., s, 2H); 7.79-7.91 (2×arom., m, 2H); 8.02-8.07 (arom., m, 1H); 8.10 (arom., d, 1H, $^3J_{HH}$=7 Hz); 8.15-8.20 (arom., m, 1H); 8.23 (arom., d, 1H, $^3J_{HH}$=7 Hz). $^{13}C\{^1H\}$ NMR ($D_2O$ with internal dioxane reference, 25° C., 125 MHz): 21.3 ($CH_2$—$CH_2$—$CH_2$, s); 49.8 ($CH_2$—arom., s); 49.8 (cycle, bs); 51.2 (cycle, s); 51.5 (cycle, s); 51.5 (cycle, s); 52.4 (cycle, s); 52.4 ($CH_2$—COOH, bs); 52.5 (cycle, s); 53.6 ($CH_2$—COOH, s); 53.6 (cycle, s); 54.1 (cycle, s); 55.1 ($CH_2$—COOH, s); 123.3 (arom., s); 126.9 (arom., s); 128.2 (arom., s); 128.4 (arom., s); 131.2 (arom., s); 131.4 (arom., s); 131.4 (arom., s); 135.1 (arom., s); 138.9 (arom., s); 170.7 (CO, bs); 172.8 (CO, s); 173.3 (CO, s).

HRMS (ESI) m/z: [(M+Na)$^+$] ($C_{25}H_{35}N_5O_7Na$) calculated: 540.2429, found: 540.2429.

Elem. analysis: M·1.5TFA·2.9$H_2O$, calculated: C (45.4), H (5.8), N (9.5), F (11.5), found: C (45.5), H (5.1), N (9.1), F (11.3).

Example 7: 1-((4,8,11-tris(carboxymethyl)-1,4,8,11-tetraazacyclotetradecan-1-yl)methyl)isoquinoline 2-oxide (7)

Starting compound D (67.3 mg, 0.336 mmol) was suspended in acetonitrile (10 mL) and 1-(bromomethyl)isoquinoline 2-oxide (40 mg, 0.168 mmol) was added and the mixture was stirred at room temperature for 24 h. The mixture was concentrated on rotary evaporator and the residue was purified on preparative HPLC ($C_{18}$ column, acetonitrile/water gradient with 0.1% TFA in the mobile phase). Fractions containing the mono-alkylated intermediate (m/z for [M+H]$^+$=358) were pooled, evaporated on rotary evaporator and dried in high vacuum. The residue was dissolved in acetonitrile (4 mL), cesium carbonate (204 mg, 0.625 mmol) was added and the mixture was stirred for 10 min at room temperature. Then, tert.butyl bromoacetate (71.1 mg, 0.365 mmol) was added and the mixture was stirred at room temperature for 72 h. The solids were filtered off and the filtrate was concentrated on rotary evaporator. Resulting oil was purified on preparative HPLC ($C_{18}$ column, acetonitrile/water gradient with 0.1% TFA in the mobile phase). Fractions containing the product in the form of tert.butyl ester were pooled, evaporated on rotary evaporator and dried in high vacuum. The residue was dissolved in neat TFA (2 mL) and the mixture was stirred for 24 h at room temperature. TFA was evaporated on rotary evaporator, the residue dissolved in distilled water (2 mL) and purified on preparative HPLC (same conditions as above). Fractions containing the product were pooled and evaporated. The residue was dissolved in distilled water (2 mL) and lyophilized, giving 30.2 mg of the product as a white fluffy solid (0.038 mmol, 23% yield relative to 1-(bromomethyl)isoquinoline 2-oxide).

$^1$H NMR (D$_2$O with internal dioxane reference, 25° C., 500 MHz): $\delta_H$ 1.81-1.91 (CH$_2$—CH$_2$—CH$_2$, m, 2H); 1.91-2.01 (CH$_2$—CH$_2$—CH$_2$, m, 2H); 2.55-2.77 (cycle CH$_2$, m, 2H); 2.97-3.08 (cycle CH$_2$, m, 2H); 3.08-3.29 (5×cycle CH$_2$, m, 10H); 3.29-3.42 (cycle CH$_2$, m, 2H); 3.54 (CH$_2$—COOH, s, 2H); 3.64 (CH$_2$—COOH, s, 2H); 3.72 (CH$_2$—COOH, s, 2H); 4.72 (CH$_2$—arom., s, 2H); 7.75-7.85 (2×arom., m, 2H); 7.96-8.01 (arom., m, 1H); 8.03 (arom., d, 1H, $^3J_{HH}$=7 Hz); 8.15-8.20 (arom., m, 1H); 8.21 (arom., d, 1H, 3J$_{HH}$=7 Hz). $^{13}$C{$^1$H} NMR (D$_2$O with internal dioxane reference, 25° C., 125 MHz): 21.0 (CH$_2$—CH$_2$—CH$_2$, s); 21.1 (CH$_2$—CH$_2$—CH$_2$, s); 48.3 (CH$_2$—arom., s); 48.3 (cycle, s); 49.9 (cycle, s); 50.6 (cycle, s); 50.7 (cycle, s); 51.0 (cycle, s); 51.1 (cycle, s); 52.7 (CH$_2$—COOH, bs); 53.1 (cycle, s); 53.2 (cycle, s); 54.0 (CH$_2$—COOH, s); 54.2 (CH$_2$—COOH, s); 123.6 (arom., s); 126.5 (arom., s); 128.1 (arom., s); 128.6 (arom., s); 131.1 (arom., s); 131.1 (arom., s); 131.2 (arom., s); 134.6 (arom., s); 141.2 (arom., s); 171.5 (CO, s); 171.9 (CO, s); 172.1 (CO, s).

HRMS (ESI) m/z: [(M+H)$^+$] (C$_{26}$H$_{38}$N$_5$O$_7$) calculated: 532.2766, found: 532.2764.

Elem. analysis: M·2.1TFA·1.6H$_2$O, calculated: C (45.3), H (5.3), N (8.8), F (15.0), found: C (45.5), H (4.6), N (8.3), F (14.6).

Example 8: 2,2',2''-(11-((6-chloropyridin-2-yl)methyl)-1,4,8,11-tetraazacyclotetradecane-1,4,8-triyl)triacetic acid (8)

The compound was prepared by a procedure analogous to Example 7, using the following amounts: starting compound D (80 mg, 0.399 mmol), 2-(bromomethyl)-6-chloropyridine (41.2 mg, 0.199 mmol); in the second step: cesium carbonate (294 mg, 0.901 mmol) and tert.butyl bromoacetate (103 mg, 0.526 mmol). Following the procedure in Example 7, analogously 27.3 mg of the product as a white fluffy solid was prepared (0.036 mmol, 18% yield relative to 2-(bromomethyl)-6-chloropyridine).

$^1$H NMR (D$_2$O with internal dioxane reference, 25° C., 500 MHz): $\delta_H$ 1.87-2.04 (2×CH$_2$—CH$_2$—CH$_2$, m, 4H); 2.80-3.02 (2×cycle CH$_2$, m, 4H); 3.05-3.16 (2×cycle CH$_2$, m, 4H); 3.22-3.41 (4×cycle CH$_2$, m, 8H); 3.54 (2×CH$_2$—COOH, s, 4H); 3.78 (CH$_2$—COOH, s, 2H); 4.30 (CH$_2$—arom., s, 2H); 7.37 (arom., d, 1H, $^3J_{HH}$=8 Hz); 7.43 (arom., d, 1H, $^3J_{HH}$=8 Hz); 7.80 (arom., t, 1H, $^3J_{HH}$=8 Hz). $^{13}$C{$^1$H} NMR (D$_2$O with internal dioxane reference, 25° C., 125 MHz): 21.9 (CH$_2$—CH$_2$—CH$_2$, s); 22.0 (CH$_2$—CH$_2$—CH$_2$, s); 50.4 (cycle, s); 50.7 (cycle, s); 51.4 (cycle, s); 51.8 (cycle, s); 51.9 (cycle, s); 52.3 (cycle, s); 53.0 (cycle, s); 53.2 (cycle, s); 54.2 (CH$_2$—COOH, s); 54.4 (CH$_2$—COOH, s); 54.7 (CH$_2$—COOH, s); 56.9 (CH$_2$—arom., s); 123.3 (arom., s); 124.9 (arom., s); 141.2 (arom., s); 150.6 (arom., s); 152.0 (arom., s); 170.9 (CO, s); 173.4 (CO, s); 173.5 (CO, s).

HRMS (ESI) m/z: [(M+H)$^+$] (C$_{22}$H$_{35}$N$_5$O$_6$C$_1$) calculated: 500.2270, found: 500.2264.

Elem. analysis: M·2.0TFA·1.9H$_2$O, calculated: C (41.0), H (5.3), N (9.2), F (15.0), Cl (4.7), found: C (41.1), H (4.6), N (8.9), F (14.6), Cl (4.8).

Example 9: 2,2',2''-(11-((6-methylpyridin-2-yl)methyl)-1,4,8,11-tetraazacyclotetradecane-1,4,8-triyptriacetic acid (9)

The compound was prepared by a procedure analogous to Example 7, using the following amounts: starting compound D (80 mg, 0.399 mmol), 2-(chloromethyl)-6-methylpyridine hydrochloride (35.6 mg, 0.199 mmol); in the second step: cesium carbonate (232 mg, 0.711 mmol) and tert.butyl bromoacetate (80.9 mg, 0.415 mmol). Following the procedure in Example 7, analogously 21.4 mg of the product as a white fluffy solid was prepared (0.027 mmol, 14% yield relative to 2-(chloromethyl)-6-methylpyridine hydrochloride).

$^1$H NMR (D$_2$O with internal dioxane reference, 25° C., 500 MHz): $\delta_H$ 1.87-2.07 (2×CH$_2$—CH$_2$—CH$_2$, m, 4H); 2.53-2.62 (cycle CH$_2$, m, 2H); 2.70 (CH$_3$, s, 3H); 2.73-2.84 (cycle CH$_2$, m, 2H); 2.89-3.08 (2×cycle CH$_2$, m, 4H); 3.15-3.29 (cycle CH$_2$, m, 2H); 3.31-3.59 (3×cycle CH$_2$+

CH$_2$—COOH, 8H); 3.86 (2×CH$_2$—COOH, s, 4H); 3.96 (CH$_2$—arom., bs, 2H); 7.71 (arom., d, 1H, $^3J_{HH}$=8 Hz); 7.76 (arom., d, 1H, $^3J_{HH}$=8 Hz); 8.32 (arom., t, 1H, $^3J_{HH}$=8 Hz). $^{13}$C{$^1$H} NMR (D$_2$O with internal dioxane reference, 25° C., 125 MHz): 19.0 (CH$_3$, s); 21.7 (CH$_2$—CH$_2$—CH$_2$, s); 22.3 (CH$_2$—CH$_2$—CH$_2$, s); 47.3 (cycle, s); 48.6 (cycle, s); 50.9 (cycle, s); 51.8 (cycle, s); 51.8 (cycle, s); 52.1 (cycle, s); 52.6 (cycle, s); 52.8 (cycle, s); 54.7 (CH$_2$—COOH, s); 54.9 (CH$_2$—arom., s); 55.2 (CH$_2$—COOH, s); 55.4 (CH$_2$—COOH, s); 124.9 (arom., s); 127.1 (arom., s); 146.5 (arom., s); 151.0 (arom., s); 154.8 (arom., s); 169.4 (CO, s); 169.5 (CO, s); 174.7 (CO, s).

HRMS (ESI) m/z: [(M+H)$^+$] (C$_{23}$H$_{38}$N$_5$O$_6$) calculated: 480.2817, found: 480.2810.

Elem. analysis: M·2.7TFA·0.8H$_2$O, calculated: C (42.5), H (5.2), N (8.7), F (19.2), found: C (42.5), H (4.9), N (8.6), F (19.3).

Example 10: 14(4,7-bis(carboxymethyl)-1,4,7-tri-azonan-1-yl)methypisoquinoline 2-oxide (10)

Starting compound B (54.6 mg, 0.153 mmol) and 1-(bromomethyl)isoquinoline 2-oxide (40 mg, 0.168 mmol) were dissolved together in acetonitrile (4 mL) and stirred for 24 hours at room temperature. The solvent was evaporated on rotary evaporator and the resulting oil was purified on preparative HPLC (C$_{18}$ column, acetonitrile/water gradient with 0.1% TFA in the mobile phase). Fractions containing the product in the form of tert.butyl ester were pooled, evaporated on rotary evaporator and dried in high vacuum. The residue was dissolved in neat TFA (2 mL) and the mixture was stirred for 24 h at room temperature. TFA was evaporated on rotary evaporator, the residue dissolved in distilled water (2 mL) and purified on preparative HPLC (same conditions as above). Fractions containing the product were pooled and evaporated. The residue was dissolved in distilled water (2 mL) and lyophilized, giving 54.6 mg of the product as a off-white fluffy solid (0.092 mmol, 60% yield relative to B).

$^1$H NMR (D$_2$O with internal dioxane reference, 25° C., 500 MHz): 6H 3.15-3.37 (6×cycle CH$_2$, m, 12H); 3.67 (CH$_2$—COOH, s, 4H); 4.89 (CH$_2$—arom., s, 2H); 7.73-7.84 (2×arom., m, 2H); 7.94-7.99 (arom., m, 1H); 8.01 (arom., d, 1H, $^3J_{HH}$=7 Hz); 8.12-8.16 (arom., m, 1H); 8.17 (arom., d, 1H, $^3J_{HH}$=7 Hz). $^{13}$C{$^1$H} NMR (D$_2$O with internal dioxane reference, 25° C., 125 MHz): 49.7 (cycle, s); 49.9 (cycle, s); 50.3 (cycle, s); 50.5 (CH$_2$—arom., s); 56.5 (CH$_2$—COOH, s); 123.5 (arom., s); 126.5 (arom., s); 128.0 (arom., s); 128.3 (arom., s); 131.1 (arom., s); 131.1 (arom., s); 131.1 (arom., s); 134.8 (arom., s); 141.0 (arom., s); 172.1 (CO, s).

HRMS (ESI) m/z: [(M+H)$^+$] (C$_{20}$H$_{27}$N$_4$O$_5$) calculated: 403.1976, found: 403.1973.

Elem. analysis: M·1.7TFA, calculated: C (47.1), H (4.7), N (9.4), F (16.3), found: C (47.6), H (4.6), N (9.4), F (16.1).

Example 11: 14(5,9-bis(carboxymethyl)-1,5,9-tri-azacyclododecan-1-yl)methypisoquinoline 2-oxide (11)

The compound was prepared by a procedure analogous to Example 7, using the following amounts: starting compound F (19.6 mg, 0.115 mmol), 1-(bromomethyl)isoquinoline 2-oxide (20 mg, 0.084 mmol) in acetonitrile (2 mL); in the second step: cesium carbonate (79 mg, 0.243 mmol) and tert.butyl bromoacetate (23.7 mg, 0.122 mmol). Following the procedure in Example 7, analogously 8.3 mg of the product as a white fluffy solid was prepared (0.013 mmol, 15% yield relative to 1-(bromomethyl)isoquinoline 2-oxide).

$^1$H NMR (D$_2$O with internal dioxane reference, 25° C., 500 MHz): 6H 1.86-2.09 (CH$_2$—CH$_2$—CH$_2$, m, 2H); 2.09-2.31 (CH$_2$—CH$_2$—CH$_2$, m, 4H); 2.89-3.51 (6×cycle CH$_2$, m, 12H); 3.63 (CH$_2$—COOH, s, 4H); 5.11 (CH$_2$—arom., s, 2H); 7.79-7.91 (2×arom., m, 2H); 8.00-8.07 (arom., m, 1H); 8.12 (arom., d, 1H, $^3J_{HH}$=7 Hz); 8.14-8.18 (arom., m, 1H); 8.26 (arom., d, 1H, $^3J_{HH}$=7 Hz). $^{13}$C{$^1$H} NMR (D$_2$O with internal dioxane reference, 25° C., 125 MHz): 19.7 (CH$_2$—CH$_2$—CH$_2$, s); 20.1 (CH$_2$—CH$_2$—CH$_2$, s); 48.8 (cycle, s); 50.8 (CH$_2$—arom., s); 50.8 (cycle, bs); 53.2 (cycle, bs); 55.1 (CH$_2$—COOH, s); 123.2 (arom., s); 127.1 (arom., s); 128.2 (arom., s); 128.3 (arom., s); 131.4 (arom., s); 131.6 (arom., s); 131.7 (arom., s); 134.6 (arom., s); 138.3 (arom., s); 172.0 (CO, s).

HRMS (ESI) m/z: [(M+H)$^+$] (C$_{23}$H$_{33}$N$_4$O$_5$) calculated: 445.2446, found: 445.2445.

Elem. analysis: M·1.6TFA·1.4H$_2$O, calculated: C (48.2), H (5.6), N (8.6), F (14.0), found: C (48.5), H (5.3), N (8.5), F (13.7).

Example 12: 14(4,8,12-tris(carboxymethyl)-1,4,8,12-tetraazacyclopentadecan-1-yl)methyl)isoquinoline 2-oxide (12)

The compound was prepared by a procedure analogous to Example 5, using starting compound E (108 mg, 0.504 mmol) and 1-(bromomethyl)isoquinoline 2-oxide (60 mg, 0.252 mmol) in acetonitrile (10 mL). Following separation on preparative HPLC as in the Example 5, only the major isomer of mono-alkylated intermediate (m/z for [M+H]$^+$= 372) was collected. Analogously to Example 5, the second reaction step was performed with the following amounts: cesium carbonate (309 mg, 0.948 mmol) and tert.butyl bromoacetate (108 mg, 0.553 mmol). Further following the procedure in Example 5, analogously 20.6 mg of the product as a white fluffy solid was prepared (0.023 mmol, 9% yield relative to 1-(bromomethyl)isoquinoline 2-oxide).

$^1$H NMR (D$_2$O with internal dioxane reference, 25° C., 500 MHz): 6H 1.95-2.09 (CH$_2$—CH$_2$—CH$_2$, m, 2H); 2.09-2.24 (2×CH$_2$—CH$_2$—CH$_2$, m, 4H); 2.87-2.97 (cycle CH$_2$, m, 2H); 3.11-3.28 (3×cycle CH$_2$, m, 6H); 3.29-3.46 (4×cycle CH$_2$+CH$_2$—COOH, 10H); 3.88 (CH$_2$—COOH, s, 2H); 3.99 (CH$_2$—COOH, s, 2H); 4.96 (CH$_2$—arom., s, 2H); 7.78-7.89 (2×arom., m, 2H); 8.01-8.06 (arom., m, 1H); 8.10 (arom., d, 1H, $^3J_{HH}$=7 Hz); 8.16-8.21 (arom., m, 1H); 8.27 (arom., d, 1H, $^3J_{HH}$=7 Hz). $^{13}$C{$^1$H} NMR (D$_2$O with internal dioxane reference, 25° C., 125 MHz): 18.6 (CH$_2$—CH$_2$—CH$_2$, s); 21.2 (CH$_2$—CH$_2$—CH$_2$, s); 22.0 (CH$_2$—CH$_2$—CH$_2$, s); 50.1 (cycle, s); 50.2 (cycle, s); 50.4 (CH$_2$—arom., s); 50.4 (cycle, s); 50.4 (cycle, s); 51.1 (cycle, s); 51.4 (cycle, s); 51.6 (cycle, s); 52.1 (cycle, s); 54.2 (CH$_2$—COOH, s); 56.2 (CH$_2$—COOH, s); 56.3 (CH$_2$—COOH, s); 123.4 (arom., s); 127.0 (arom., s); 128.2 (arom., s); 128.4 (arom., s); 131.2 (arom., s); 131.4 (arom., s); 131.4 (arom., s); 134.9 (arom., s); 139.7 (arom., s); 168.4 (CO, s); 168.5 (CO, s); 172.3 (CO, s).

HRMS (ESI) m/z: [(M+H)$^+$] (C$_{27}$H$_{40}$N$_5$O$_7$) calculated: 546.2922, found: 546.2920.

Elem. analysis: M·2.8TFA·2.2H$_2$O, calculated: C (43.3), H (5.1), N (7.7), F (17.6), found: C (43.5), H (4.4), N (7.3), F (17.1).

II Separation of s-, p- and d-block Metals

The chelator molecules described in this invention were tested for their ability to separate s-, p- and d-block metals by first forming chelates with a chelator that provides chromatographic selectivity towards the metals and then subjecting the chelates to conventional chromatographic separation.

Example 13: Variability in retention of metal chelates on reversed-phase HPLC usable for separation Complexation of selected s-, p- and d-block metals (Ca$^+$, Fe$^+$, Fe$^+$, Co$^+$, Ni$^{2+}$, Zn$^{2+}$, Al$^{3+}$, Pb$^{2+}$) were carried out in parallel in 96-well plates as follows. MOPS buffer pH=7.0 (85 μL), approximately 0.01 M aqueous solution of the chelator (5 μL), and approximately 0.005 M aqueous solution of a metal salt of a composition given in Table 1 (10 μL) were pipetted into a well. The well-plate was covered with a pierceable sealing mat, shaken well for complete mixing of the components and let stand for 16 hour at room temperature. After that it was shaken again and briefly centrifugated to bring all liquid to the well bottom. Samples for HPLC analysis were taken directly from the wells with an automated autosampler. The conditions for HPLC analysis were as follows: column Phenomenex Kinetex C$_{18}$ (100×3 mm, 2 6 lam), injection volume 1 μL, isocratic elution with a mobile phase as specified in Table 1, flow rate of 0.6 mL/min and detection by UV absorbance at 280 nm. Retention times for respective metal chelates are summarized in Table 1. For a given chelator, differing retention times of different metals signify that such metals can be chromatographically separated in the form of chelates with that chelator. The results in Table 1 demonstrate that various combinations of metals from the s-, p- and d-block can be separated according to the present invention.

TABLE 1

| | | Compound (chelator) | | |
| | | 8 $^a$ | 10 $^b$ | 11 $^c$ |
| Metal ion | Metal compound | Retention time (minutes) | | |
| --- | --- | --- | --- | --- |
| Co$^{2+}$ | Co(NO$_3$)$_2$ | 4.58 | 2.60 | 2.74 |
| Ni$^{2+}$ | Ni(NO$_3$)$_2$ | 4.47 | 2.56 | 2.87 |
| Cu$^{2+}$ | CuCl$_2$ | 1.9 | 3.18 | 2.74 |
| Zn$^{2+}$ | Zn(NO$_3$)$_2$ | 3.18 | 3.48 | 2.29 |
| Pb$^{2+}$ | Pb(NO$_3$)$_2$ | (1.15) * | 3.41 | 1.30 |

* Metal chelate unstable under the conditions, only free chelator detected (value in parentheses).
$^a$ Eluent: 8% acetonitrile in 10 mM α-HIBA (pH = 5.5).
$^b$ Eluent: 4.6% acetonitrile in water.
$^c$ Eluent: 11% acetonitrile in water.

III Separation of Rare Earth Elements

The chelator molecules described in this invention were tested for their ability to separate rare earth elements by first forming chelates with a chelator that provides chromatographic selectivity towards rare earth elements and then subjecting the chelates to conventional chromatographic separation.

Example 14: Variability in Retention of Metal Chelates on Reversed-phase HPLC Usable for Separation Solutions of metal chelates were prepared according to the procedure in Example 13 with the following pipetted amounts: MOPS buffer pH=7.0 (90 μL), 0.01 M solution of chelator (5 pi) and 0.01 M solution of metal chloride or nitrate (5 μL). The conditions for HPLC analysis were identical to those in Example 13 except for the composition of the mobile phase as specified in Table 2. Retention times for respective metal chelates are summarized in Table 2. For a given chelator, differing retention times of different metals signify that such metals can be chromatographically separated in the form of chelates with that chelator. The results in Table 2 demonstrate that various combinations of metals from the rare earth element group can be separated according to the present invention.

TABLE 2

| | Compound (chelator) | | |
| | 5 $^a$ | 6 $^b$ | 10 $^c$ |
| Metal ion | Retention time (minutes) | | |
| --- | --- | --- | --- |
| La$^{3+}$ | 3.69 | 3.82 | 3.65 |
| Ce$^{3+}$ | 3.78 | 4.14 | 3.64 |
| Pr$^{3+}$ | 3.83 | 4.35 | 3.60 |
| Nd$^{3+}$ | 3.73 | 4.43 | 3.51 |
| Sm$^{3+}$ | 3.37 | 4.62 | 3.67 |
| Eu$^{3+}$ | 2.97 | 4.62 | 3.67 |

TABLE 2-continued

| | Compound (chelator) | | |
|---|---|---|---|
| | 5 [a] | 6 [b] | 10 [c] |
| Metal ion | Retention time (minutes) | | |
| $Gd^{3+}$ | 2.58 | 4.43 | 3.48 |
| $Tb^{3+}$ | 2.21 | 3.67 | 3.38 |
| $Dy^{3+}$ | 2.12 | 3.06 | 3.25 |
| $Ho^{3+}$ | 2.07 | 2.60 | 3.09 |
| $Er^{3+}$ | 2.05 | 2.35 | 3.03 |
| $Tm^{3+}$ | 2.10 | 2.29 | 3.03 |
| $Yb^{3+}$ | 2.10 | 2.25 | 3.05 |
| $Lu^{3+}$ | 2.07 | 2.20 | 2.98 |
| $Y^{3+}$ | 2.08 | 2.67 | 3.15 |
| $Sc^{3+}$ | 2.54 | 2.58 | 4.17 |

[a] Eluent: 6.2% acetonitrile in water.
[b] Eluent: 7.4% acetonitrile in water.
[c] Eluent: 4.6% acetonitrile in 10 mM α-HIBA (pH = 5.5).

Example 15: HPLC Separation of Gd, Tb and Dy from a Mixture

Figure 1:
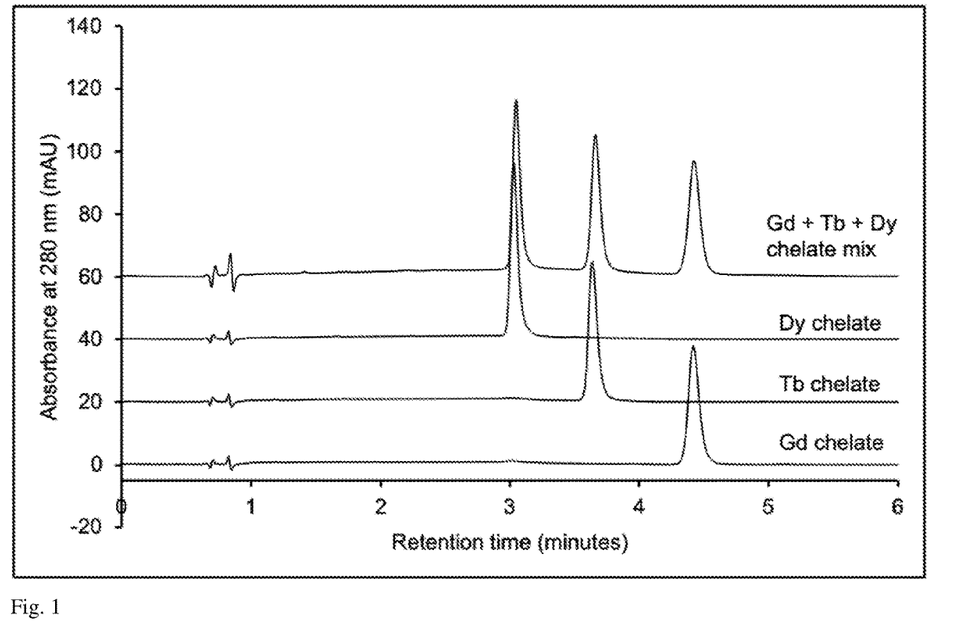
FIG. 1: A stack of HPLC chromatograms of Gd, Tb and Dy chelates of a single chelator subjected to HPLC analysis individually (bottom three) and in a mixture (top) as described in Example 15. A baseline separation of all three metal chelates was achieved.

Solutions of Gd, Tb and Dy chelates were prepared according to the procedure in Example 14 with the chelator 14(4,7,10-tris(carboxymethyl)-1,4,7,10-tetraazacyclotridecan-1-yl)methyl)isoquinoline 2-oxide (prepared in Example 6). The chelates were subjected to HPLC analysis individually and as a mixture. The conditions for HPLC analysis were identical to those in Example 13 except for the composition of the mobile phase that consisted of 7.4% acetonitrile in water with no additives. FIG. 1 shows that baseline separation of all three chelates from the mixture was successfully achieved.

Example 16: Acidic Decomplexation and Removal of the Free Chelator

Figure 2:
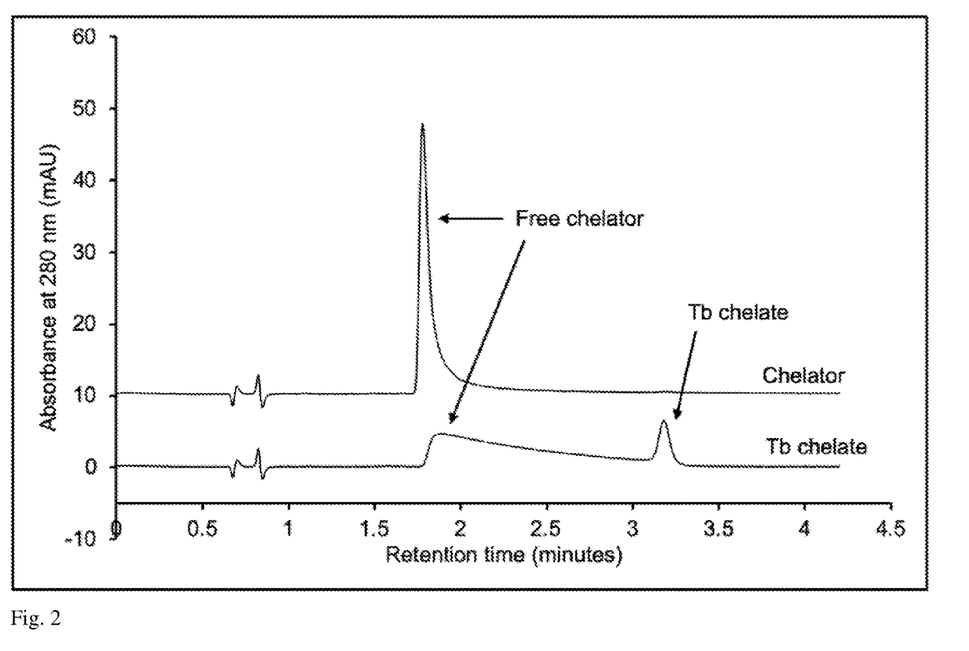
FIG. 2: A stack of HPLC chromatograms showing a decomplexation of a Tb chelate (bottom) under acidic condition as described in Example 16 and its comparison with the same free chelator (top) under the same conditions. The presence of the peak of the free chelator in the chromatogram of the Tb chelate confirms significant decomplexation of the chelate into free chelator and free metal ions.

Solution of Tb chelate of the chelator 14(4,7,10-tris (carboxymethyl)-1,4,7,10-tetraazacyclotridecan-1-yl) methyl)isoquinoline 2-oxide (prepared in Example 6) was prepared according to procedure in Example 14 and subjected to HPLC analysis using an acidic mobile phase. The conditions for HPLC analysis were identical to those in Example 13 except for the composition of the mobile phase that consisted of 7.4% acetonitrile and 0.02% of TFA in water. FIG. 2 shows chromatogram of this analysis overlaid with a chromatogram of the free chelator under the same conditions. There was apparent (partial) decomplexation of the metal chelate to free chelator (visible by UV absorbance) and free Tb ions (not visible by UV absorbance) due to the acidic mobile phase. These results confirm that the metal chelate can be decomposed to free metal ions and a free chelator under acidic conditions, and that the chelator (having retention on the column) can be chromatographically removed from the metal ions (that have no retention on the column).

INDUSTRIAL APPLICABILITY

The present invention is considered as susceptible of industrial application in separation and purification of metals, separation and purification of metal radionuclides, concentrating diluted solutions of metal radionuclides by means of solid phase extraction, recovery of isotopically enriched metal material used for production of metal radionuclides, purification of starting metal material prior to its use for production of metal radionuclides, decontamination of surfaces contaminated by metal radionuclides, selective recovery of metals from nuclear waste, selective recovery of metals from products of nuclear fission, hydrometallurgical processing of spent nuclear fuel and other radioactive waste.

The invention claimed is:

1. A method of chromatographic separation comprising:
providing a mixture of at least one metal ion selected from Ce, Dy, Er, Eu, Gd, Ho, La, Lu, Nd, Pr, Pm, Sm, Sc, Tb, Tm, Yb, Y, alkaline earth metals, Al, Ga, In, Tl, Sn, Pb, Bi and transitional metals, and at least one further metal ion, wherein said further metal ion is selected from rare earth metal ions, transition metal ions, non-transition metal ions, and actinide ions,
contacting the mixture with at least one compound of general formula (I) to form a chelates;
applying the chelates to a chromatographic column; and
eluting from the chromatographic column a chelate of the at least one metal ion and a chelate of the at least one further metal ion;
wherein:
formula (I) is:

(I)

X is H, $C_1$ to $C_6$ alkyl, F, Cl, Br or I;
Y is N or N-oxide;
$Z^1$, $Z^2$, and $Z^m$, wherein m is 1 or 2, are $-CH_2-CH_2-$ or $-CH_2-CH_2-CH_2-$;
A and $A^m$, wherein m is 1 or 2, are independently H, $-CH_2COOH$, $-CH_2C(O)NH_2$;
$-CH_2P(O)(OH)_2$, or n is 1 or 2;
$R^1$, $R^2$, and $R^3$ are independently H, $C_1$ to $C_6$ alkyl, $C_1$ to $C_6$ alkyloxy, $C_6$ to $C_{10}$ aryloxy, benzyloxy, $C_1$ to $C_6$ alkylthio, $C_6$ to $C_{10}$ arylthio, F, Cl, Br, I, OH, SH, $NH_2$, $C_1$ to $C_6$ alkylamino, di ($C_1$ to $C_6$ alkyl) amino, $C_1$ to $C_6$ acylamino, di($C_1$ to $C_6$ acyl) amino, $C_6$ to $C_{10}$ arylamino, di($C_6$ to $C_{10}$ aryl) amino, CN, OH, nitro, $COOR_n$, $C(O)NHR_n$, or $C(O)N(R_n)_2$, wherein $R_n$ is independently H, $C_1$ to $C_{10}$ alkyl, or $C_6$ to $C_{10}$ aryl;
and/or wherein any neighboring two of $R^1$, $R^2$, and $R^3$ together with any neighboring two carbon atoms of the aromatic cycle form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl) amino, NO$_2$, COOH, COOR$_n$, C(O)NHR$_n$, or C(O)N(R$_n$)$_2$, wherein Rn is independently H, C$_1$ to C$_{10}$ alkyl, C$_6$ to C$_{10}$ aryl;
with the proviso that when n is 2 and all of Z$^1$, Z$^2$, Z$^m$ are -CH$_2$-CH$_2$-, then A is not -CH$_2$COOH.

2. The method of claim 1,
wherein the at least one metal ion comprises Ce, Dy, Er, Eu, Gd, Ho, La, Lu, Nd, Pr, Pm, Sm, Sc, Tb, Tm, Yb, and Y, and the
at least one further metal ion is selected from rare earth metal ions, transition metal ions, non-transition metal ions, and actinide ions.

3. The method of claim 1 further comprising, repeating the applying and eluting steps to further separate the at least one metal ion.

4. The method of claim 1 further comprising decomplexing with acid the chelate of the metal ion to obtain the metal ion.

5. The method of claim 1, wherein the at least one metal ion is Ce, Dy, Er, Eu, Gd, Ho, La, Lu, Nd, Pr, Pm, Sm, Sc, Tb, Tm, Yb, or Y.

6. The method of claim 5, wherein the at least one further metal ion is different from the at least one metal ion and is Ce, Dy, Er, Eu, Gd, Ho, La, Lu, Nd, Pr, Pm, Sm, Sc, Tb, Tm, Yb, or Y.

7. The method of claim 1, wherein the at least one metal ion and the at least one further metal ion are s-, p-and d-block metals, selected from groups II.A, III.A, IV.A, V.A, I.B, II.B, and VIII.B metal.

8. The method of claim 7, wherein the at least one metal ion and the at least one further metal ion are different and are Ca$^{2+}$, Fe$^{2+}$, Fe$^{3+}$, Co$^{2+}$, Ni$^{2+}$, Cu$^{2+}$, Zn$^{2+}$, Al$^{3+}$, Pb$^{2+}$, or Bi$^{3+}$.

9. The method of claim 1, wherein X is H, -CH$_3$, or Cl.

10. The method of claim 1, wherein R$^1$, R$^2$, and R$^3$ are independently H, C$_1$ to C$_6$ alkyl, and/or neighboring two of R$^1$, R$^2$, R$^3$ together with neighboring two carbon atoms of the aromatic cycle form a six-membered ring, optionally substituted with one or more substituents independently selected from the group consisting of OH, SH, CF$_3$, F, Cl, Br, I, C$_1$ to C$_6$ alkyl, C$_1$ to C$_6$ alkyloxy, C$_1$ to C$_6$ alkylthio, NH$_2$, C$_1$ to C$_6$ alkylamino, di(C$_1$ to C$_6$ alkyl) amino, NO$_2$, COOH, COOR$_n$, C(O)NHR$_n$, and C(O)N(R$_n$)$_2$, wherein R$_n$ is independently H or C$_1$ to C$_{10}$ alkyl or C$_6$ to C$_{10}$ aryl.

11. The method of claim 1, wherein at most one of A and A$^m$ is H.

12. The method of claim 1, wherein X is -CH$_3$ or Cl, Y is N, and all of R$^1$, R$^2$, and R$^3$ are H.

13. The method of claim 1, wherein X is H, Y is N-oxide, and two of R$^1$, R$^2$, and R$^3$ together with neighboring two carbon atoms of the aromatic cycle form a six-membered ring, optionally substituted with one or more substituents independently selected from the group consisting of OH, SH, CF$_3$, F, Cl, Br, I, C$_1$ to C$_6$ alkyl, C$_1$ to C$_6$ alkyloxy, C$_1$ to C$_6$ alkylthio, NH$_2$, C$_1$ to C$_6$ alkylamino, di(C$_1$ to C$_6$ alkyl) amino, NO$_2$, COOH, COOR$_n$, C(O)NHR$_n$, and C(O)N(R$_n$)$_2$, wherein R$_n$ is independently H or C$_1$ to C$_{10}$ alkyl or C$_6$ to C$_{10}$ aryl.

14. The method of claim 1, wherein the compound represented by formula (I) is: 1-((4,7-bis (carboxymethyl)-1,4,7,10-tetraazacyclododecan-1-yl) methyl) isoquinoline 2 oxide; 1-((4-(2-amino-2-oxoethyl)-7,10-bis (carboxymethyl)-1,4,7,10-tetraazacyclododecan-1-yl) methyl) isoquinoline 2-oxide; 1-((4,10-bis (2-amino-2-oxoethyl)-7-(phosphonomethyl)-1,4,7,10-tetraazacyclododecan-1-yl) methyl) isoquinoline 2-oxide; 1,1'-((7,10-bis (carboxymethyl)-1,4,7,10-tetraazacyclododecane-1,4 diyl) bis (methylene)) bis (isoquinoline 2-oxide); 1-((1,7,10-tris (carboxymethyl)-1,4,7,10-tetraazacyclotridecan-4-yl) methyl) isoquinoline 2-oxide; 1-((4,7,10-tris (carboxymethyl)-1,4,7,10-tetraazacyclotridecan-1-yl) methyl) isoquinoline 2-oxide; 1-((4,8,11-tris (carboxymethyl)-1,4,8,11-tetraazacyclotetradecan-1-yl) methyl) isoquinoline 2-oxide;
2,2',2''-(11-((6-chloropyridin-2-yl) methyl)-1,4,8,11-tetraazacyclotetradecane-1,4,8-triyl) triacetic acid; 2,2', 2''-(11-((6-methylpyridin-2-yl) methyl)-1,4,8,11-tetraazacyclotetradecane-1,4,8-triyl) triacetic acid; 1-((4, 7-bis (carboxymethyl)-1,4,7-triazonan-1-yl) methyl) isoquinoline 2-oxide; 1-((5,9-bis (carboxymethyl)-1,5, 9-triazacyclododecan-1-yl) methyl) isoquinoline 2-oxide; or 1-((4,8,12-tris (carboxymethyl)-1,4,8, 12-tetraazacyclopentadecan-1-yl) methyl) isoquinoline 2-oxide.

15. A compound represented by formula (Ia), (I)

X is H, C$_1$ to C$_6$ alkyl, F, Cl, Br or I;
Y is N or N-oxide;
Z$^1$, Z$^2$, and Z$^m$, wherein m is 1 or 2, are -CH$_2$-CH$_2$-or -CH$_2$-CH$_2$-CH$_2$-;
A and A$^m$, wherein m is 1 or 2, are independently H, -CH$_2$COOH, -CH$_2$C(O)NH$_2$; or -CH$_2$P(O)(OH)$_2$, and wherein at most one of A and A$^m$ is H;
n is 1 or 2;
R$^1$, R$^2$, and R$^3$ are independently H, C$_1$ to C$_6$ alkyl, C$_1$ to C$_6$ alkyloxy, C$_6$ to C$_{10}$ aryloxy, benzyloxy, C$_1$ to C$_6$ alkylthio, C$_6$ to C$_{10}$ arylthio, F, Cl, Br, I, OH, SH, NH$_2$, C$_1$ to C$_6$ alkylamino, di(C$_1$ to C$_6$ alkyl) amino, C$_1$ to C$_6$ acylamino, di(C$_1$ to C$_6$ acyl)amino, C$_6$ to C$_{10}$ arylamino, di(C$_6$ to C$_{10}$ aryl)amino, CN, OH, nitro, COOR$_n$, C(O)NHR$_n$, or C(O)N(R$_n$)$_2$, wherein R$_n$ is independently H, C$_1$ to C$_{10}$ alkyl, or C$_6$ to C$_{10}$ aryl;
and/or wherein any neighboring two of R$^1$, R$^2$, and R$^3$ together with any neighboring two carbon atoms of the aromatic cycle form a six-membered ring, optionally substituted with one or more substituents independently selected from the group consisting of OH, SH, CF$_3$, F, Cl, Br, I, C$_1$ to C$_6$ alkyl, C$_1$ to C$_6$ alkyloxy, C$_1$ to C$_6$ alkylthio, NH$_2$, C$_6$ to C$_{10}$ alkylamino, di(C$_6$ to C$_{10}$ alkyl) amino, NO$_2$, COOH, COOR$_n$, C(O)NHR$_n$, or C(O)N(R$_n$)$_2$, wherein R$_n$ is independently H, C$_1$ to C$_{10}$ alkyl, C$_6$ to C$_{10}$ aryl;
with the proviso that:
when n is 2, all of Z$^1$, Z$^2$, Z$^m$ are -CH$_2$-CH$_2$-, then A is not -CH$_2$COOH;
when Y is nitrogen, then X is not H; and
when n is 1, all of Z$^1$, Z$^2$, Z$^m$ are -CH$_2$-CH$_2$-, and Y is nitrogen, then X is not halogen.

16. The compound of claim 15, wherein X is selected from a group consisting of H; -CH$_3$ and Cl.

17. The compound of claim 15, wherein R$^1$, R$^2$, R$^3$ are independently H; C$_1$ to C$_6$ alkyl; and/or neighboring two of R$^1$, R$^2$, R$^3$ together with neighboring two carbon atoms of the aromatic cycle form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl) amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl.

18. The compound of claim 15 which is: 1-((4,7-bis (carboxymethyl)-1,4,7,10-tetraazacyclododecan-1-yl) methyl) isoquinoline 2-oxide; 1-((4-(2-amino-2-oxoethyl)-7,10-bis (carboxymethyl)-1,4,7,10-tetraazacyclododecan-1-yl) methyl) isoquinoline 2-oxide; 1-((4,10-bis (2-amino-2-oxoethyl)-7-(phosphonomethyl)-1,4,7,10-tetraazacyclododecan-1-yl) methyl) isoquinoline 2-oxide; 1-((1,7,10-tris (carboxymethyl)-1,4,7,10-tetraazacyclotridecan-4-yl) methyl) isoquinoline 2-oxide; 1-((4,7,10-tris (carboxymethyl)-1,4,7,10-tetraazacyclotridecan-1-yl) methyl) isoquinoline 2-oxide; 1-((4,8,11-tris (carboxymethyl)-1,4,8,11-tetraazacyclotetradecan-1-yl) methyl) isoquinoline 2-oxide; 2,2',2"-(11-((6-chloropyridin-2-yl) methyl)-1,4,8,11-tetraazacyclotetradecane-1,4,8-triyl) triacetic acid; 2,2',2"-(11-((6-methylpyridin-2-yl) methyl)-1,4,8,11-tetraazacyclotetradecane-1,4,8-triyl) triacetic acid; 1-((4,7-bis (carboxymethyl)-1,4,7-triazonan-1-yl) methyl) isoquinoline 2-oxide; 1-((5,9-bis (carboxymethyl)-1,5,9-triazacyclododecan-1-yl) methyl) isoquinoline 2-oxide; or 1-((4,8,12-tris (carboxymethyl)-1,4,8,12-tetraazacyclopentadecan-1-yl) methyl) isoquinoline 2-oxide.

\* \* \* \* \*